US012130271B2

(12) United States Patent
Thoma et al.

(10) Patent No.: US 12,130,271 B2
(45) Date of Patent: Oct. 29, 2024

(54) SYSTEMS AND METHODS FOR PLACING NETWORKED SENSORS WITHIN A FACILITY FOR FUGITIVE EMISSIONS MONITORING

(71) Applicant: MOLEX, LLC, Lisle, IL (US)

(72) Inventors: Eben Daniel Thoma, Cary, NC (US); Alexander S. Chernyshov, Naperville, IL (US); Wenfeng Peng, North Aurora, IL (US); Ling-Yin Lin, Bloomingdale, IL (US); Jingxue Xu, Chicago, IL (US)

(73) Assignee: Molex, LLC, Lisle, IL (US)

( * ) Notice: Subject to any disclaimer, the term of this patent is extended or adjusted under 35 U.S.C. 154(b) by 346 days.

(21) Appl. No.: 17/611,916

(22) PCT Filed: May 22, 2020

(86) PCT No.: PCT/US2020/034115
§ 371 (c)(1),
(2) Date: Nov. 17, 2021

(87) PCT Pub. No.: WO2020/237112
PCT Pub. Date: Nov. 26, 2020

(65) Prior Publication Data
US 2022/0205967 A1   Jun. 30, 2022

Related U.S. Application Data

(60) Provisional application No. 62/851,120, filed on May 22, 2019.

(51) Int. Cl.
*G01N 33/00* (2006.01)
*G01M 3/04* (2006.01)

(52) U.S. Cl.
CPC .......... *G01N 33/0075* (2013.01); *G01M 3/04* (2013.01); *G01N 33/0006* (2013.01)

(58) Field of Classification Search
CPC . G01N 33/0075; G01N 33/0006; G01M 3/04; H04Q 2209/40; H04Q 2209/60;
(Continued)

(56) References Cited

U.S. PATENT DOCUMENTS 7,006,889 B2    2/2006  Mathur et al.
10,785,809 B1 *  9/2020  Thubert .............. H04W 40/246
(Continued)

FOREIGN PATENT DOCUMENTS

CN      1491375 A      4/2004
CN    104349356 A      2/2015
(Continued)

OTHER PUBLICATIONS

Becker et al., "Automatic Sensor Placement in a 3D Volume", PETRA'09, Retrieved from Internet URL: https://dl.acm.org/doi/pdf/10.1145/1579114.1579150, Jun. 2009, pp. 1-8.
(Continued)

Primary Examiner — Curtis J King

(57) ABSTRACT

A gas sensor network system provides near real-time monitoring of fugitive emissions of VOC compounds in chemical plants and facilities. The present disclosure provides a sensor placement method which determines where to place sensors within a facility. The sensor placement method includes obtaining plant layout, gas composition, meteorological conditions and/or other types of information regarding a facility, determining the types of gas and ancillary sensors needed, and generating the minimum detection distances required based on the sensitivities of the sensors to the gas compounds involved. And, then calculating the minimal number of sensors required for each sensor type with optimized sensor locations to ensure best coverage of potentially leaking components within the facility.

20 Claims, 8 Drawing Sheets

502

504

(58) Field of Classification Search
CPC ............... H04Q 2209/823; H04Q 9/00; G05B 19/4183; G05B 19/4185; G05B 2219/37451; G01D 21/02; H04L 67/12
See application file for complete search history.

(56) References Cited

U.S. PATENT DOCUMENTS

| | | | |
|---|---|---|---|
| 2004/0108954 A1* | 6/2004 | Richley | G01S 5/0226 |
| | | | 342/465 |
| 2006/0070128 A1* | 3/2006 | Heimerdinger | H04L 63/1441 |
| | | | 726/23 |
| 2013/0345993 A1* | 12/2013 | Bellala | G01F 15/063 |
| | | | 702/45 |
| 2014/0061962 A1 | 3/2014 | Lane et al. | |
| 2014/0163916 A1* | 6/2014 | Ba | G06F 30/13 |
| | | | 702/100 |
| 2015/0192677 A1* | 7/2015 | Yu | G01S 17/89 |
| | | | 356/5.01 |
| 2017/0188250 A1* | 6/2017 | Stevens | H04L 41/0631 |
| 2017/0200364 A1* | 7/2017 | Shahraz | G08B 21/12 |
| 2018/0136180 A1* | 5/2018 | Chou | G01N 33/0075 |
| 2019/0043350 A1* | 2/2019 | Rosales | H04L 41/5025 |
| 2019/0306804 A1* | 10/2019 | Goli | H04W 52/242 |
| 2020/0117897 A1* | 4/2020 | Froloff | G06N 20/20 |
| 2021/0112647 A1* | 4/2021 | Coleman | H05B 47/16 |
| 2022/0406158 A1* | 12/2022 | Mahmoud | H02H 7/226 |
| 2023/0152652 A1* | 5/2023 | Trikha | H10K 59/65 |
| | | | 700/276 |
| 2023/0176023 A1* | 6/2023 | Wang | G01N 33/0063 |
| | | | 340/632 |
| 2023/0191635 A1* | 6/2023 | Vu | B25J 9/1676 |
| | | | 700/259 |
| 2023/0359162 A1* | 11/2023 | Kriveshko | G01S 17/04 |
| 2023/0393443 A1* | 12/2023 | Marquez | G05B 19/042 |

FOREIGN PATENT DOCUMENTS

| | | |
|---|---|---|
| WO | 2012168904 A2 | 12/2012 |
| WO | 2020237112 A1 | 11/2020 |

OTHER PUBLICATIONS

International Preliminary Report on Patentability received for PCT Application No. PCT/US2020/034115, mailed on Dec. 2, 2021, 10 Pages.

International Search Report and Written Opinion received for PCT Application No. PCT/US2020/034115, mailed on Sep. 10, 2020, 11 Pages.

* cited by examiner

SYSTEMS AND METHODS FOR PLACING NETWORKED SENSORS WITHIN A FACILITY FOR FUGITIVE EMISSIONS MONITORING

RELATED APPLICATIONS

This application is a national phase of PCT/US2020/034115, filed on May 22, 2020, which claims the benefit of priority to U.S. Provisional Patent Application Ser. No. 62/851,120, filed May 22, 2019, which are herein incorporated by reference in their entireties.

This invention was made with Government support under Cooperative Research and Development Agreement (CRADA) #914-16 awarded by the United States Environmental Protection Agency. The Government has certain rights in the invention.

This invention was made with Government support under Cooperative Research and Development Agreement (CRADA) #914-16 awarded by the United States Environmental Protection Agency. The Government has certain rights in the invention.

TECHNICAL FIELD

Aspects of the disclosure relate to the field of sensor network-based emissions monitoring systems, more specifically to the methods used to determine where to place sensors within a facility to best ensure detection of fugitive emissions in any location within the facility, while minimizing/reducing the number of sensors required to be placed within the facility to accomplish same.

DESCRIPTION OF RELATED ART

Volatile organic compounds ("VOCs") and hazardous air pollutants ("HAPs") can be emitted from a variety of sources in industrial facilities such as stacks, tanks, vents, and other sources as part of normal operations, and valve packing, pump seals, compressor seals, and flange gaskets as potential leak interfaces on process equipment and components. There are numerous federal, state, and local regulations designed to control fugitive emissions from industrial sources through leak detection and repair ("LDAR") work practices, which are designed to identify leaking equipment so that emissions of VOCs and HAPs can be reduced through effective repairs. Although the detailed compliance requirements can be quite complex, each LDAR regulation is essentially a variation on the theme of monitoring components to find fugitive leaks, repairing and re-monitoring those leaks in a specified time frame, and maintaining the records necessary to demonstrate compliance. Leak detection is performed by periodically monitoring each component in light liquid or gas vapor VOC service per 40 CFR Part 60 Appendix A-7, Test Method 21 ("EPA Method 21"). If the measured value (typically in parts per million by volume) exceeds the regulatory leak definition, a leak is detected. Large complex refineries and chemical facilities may be required to monitor hundreds of thousands of components each year to identify the 1-2% of the component population that are leaking.

In execution of EPA Method 21, an inspector places an extractive hand-held probe in direct contact with the component under test and traces its circumference, waiting an appropriate amount of time to register a reading of leak concentration (mixing ratio of combustible fraction). If the highest concentration reading is above a control limit, typically 500 to 2000 parts per million, then the component is tagged for repair. The EPA Method 21-determined concentrations are sometimes used to approximate mass flow rates through correlation equations to estimate annual emission leak rates for the facility—a procedure with several sources of uncertainty. It is well known that manual leak detection methods to monitor and repair sources of fugitive emissions are resource intensive and difficult to apply on hard-to-reach sources. Additionally, EPA Method 21 is expensive to execute and can produce safety concerns for inspectors. This manual inspection procedure only checks a subset of potential emissions points inside a facility and possesses high temporal latency since some components may not be visited for more than a year, creating the potential for a leak to go undetected for an extended time. On the other hand, manual placement and testing of sensors can be very costly, time consuming, and technically challenging. It may require months and several visits to the plant by experienced and/or trained personnel. Moreover, each facility/plant may have a different layout and product streams, and there are many critical parameters to consider.

In addition, artificial intelligence (AI) is of increasing interest in fields where significant human time and subjective decision-making is otherwise necessary. AI also has benefits beyond programming efficiency: machines may also learn and identify correlations in data that would otherwise go undetected if reviewed by humans. While a human would be unlikely to detect a correlation given the volume of data involved and a lack of a motivation to compare such datasets, a machine learning AI algorithm may do so largely without human intervention.

As a result of the foregoing, one or more improvements upon the various shortcomings in the prior art are desired. Manual placement and testing of sensors can be very costly, time consuming, and technically challenging. It may require months and several visits to the plant by experienced and/or trained personnel. Moreover, artificial intelligence, such as machine learning, is still nascent in many fields, and the integration of its capabilities still leaves much room for improvement.

SUMMARY

In the following description of various illustrative embodiments, reference is made to the accompanying drawings, which form a part hereof, and in which is shown, by way of illustration, various embodiments in which aspects of the disclosure may be practiced. It is to be understood that other embodiments may be utilized and structural and functional modifications may be made, without departing from the scope of the present disclosure. It is noted that various connections between elements are discussed in the following description. It is noted that these connections are general and, unless specified otherwise, may be direct or indirect, wired or wireless, and that the specification is not intended to be limiting in this respect.

In an embodiment, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method for placement of a plurality of networked sensors in a facility that transports chemical materials across a distance to detect one or more gaseous plumes resulting from leaks in the facility, the method including: storing, by an emissions monitoring apparatus in a data store, a digital representation of the facility including a plurality of components that transport the chemical materials across the distance, where the digital representation includes a plurality of zones spread across the facility; algorithmically calculating an optimal placement of a plurality of networked sensors in the digital representation of the facility to detect a gaseous plume resulting from a leak, where the optimal placement includes at least a first coordinate, a second coordinate, and a third coordinate; providing instructions to affix a plurality of networked sensors at specific coordinates in the facility, where the instructions indicate a first networked sensor is to be affixed at the first coordinate in the facility, a second networked sensor is to be affixed at the second coordinate in the facility, and a third networked sensor is to be affixed at the third coordinate in the facility; and updating the digital representation of the facility stored in the data store by replacing the first coordinate, the second coordinate, and the third coordinate with actual coordinates reported to the emissions monitoring apparatus. Other embodiments of this aspect include corresponding computer systems, apparatus, and computer programs recorded on one or more computer storage devices, each configured to perform the actions of the methods.

Implementations may include one or more of the following features. The method where the plurality of components that transport the chemical materials across the distance include: a valve component assembled between a first component and second component of the plurality of components that transport chemical materials in the facility; and a controller, which is communicatively coupled to the emissions monitoring apparatus, configured to actuate the valve component from an open position to a closed position. The method may also include: in response to the second component, which is identified as being located at least partially inside the location boundary, being a potential source of the leak, actuating, by the emissions monitoring apparatus, the controller to actuate the valve component into the closed position. The method may also include: after the plurality of networked sensors are affixed in the facility, calculating, by the emissions monitoring apparatus, the actual coordinates of each of the first networked sensor, the second networked sensor, and the third networked sensor in the facility by triangulating a wireless signal emitted by each of the first networked sensor, the second networked sensor, and the third networked sensor. The method may further include: generating, by a remote server machine, the digital representation of the facility, where the digital representation includes 3-dimensional structures, 3-dimensional openings between the 3-dimensional structures, a geographic location of the facility, the plurality of components that transport chemical materials across the distance in the facility, and a composition of the chemical materials; and updating, in near real-time, the digital representation of the facility based on current meteorological conditions measured at the facility. The method further including: measuring, in near real-time at the facility, the current meteorological conditions at the facility, where the current meteorological conditions include wind speed, wind direction, and temperature. The method where the plurality of zones include LDAR zones, and where a first zone of the plurality of zones is assigned a weight score based on at least a quantity of components located in the first zone and gas sensitivity, and where the algorithmically calculating includes: iterating through a plurality of combinations of the first coordinate, the second coordinate, and the third coordinate to identify, using artificial intelligence (ai), an optimization of a cost function based on weight scores assigned to each of the plurality of LDAR zones, where the cost function is based on at least a detection zone of each of the first networked sensor, the second networked sensor, and the third networked sensor; and where the optimization is further based on satisfying a pre-defined coverage percentage threshold for one of: individual LDAR zones, all LDAR zones, and geometric sensor location. In some examples, the cost function is further based on: a sensor type and sensitivity of each of the first networked sensor, the second networked sensor, and the third networked sensor, where the detection zone of each networked sensor is derived from its sensor type and sensitivity; and a composition of the chemical materials transported across the distance in the facility in the plurality of components. The method may perform, in some examples, where the plurality of networked sensors includes more the first networked sensor, the second networked sensor, and the third networked sensor, and where the plurality of networked sensors include a sensor assembly configured to measure the current meteorological conditions at the facility, and where the first networked sensor includes multiple sensors of more than one type. The method may perform, in some examples, after the plurality of networked sensors are affixed in the facility, by calculating the actual coordinates of each of the first networked sensor, the second networked sensor, and the third networked sensor in the facility by triangulating a wireless signal emitted by each of the first networked sensor, the second networked sensor, and the third networked sensor, where the triangulating the wireless signal includes calculating time to receive the wireless signal. The method as claimed, where the algorithmically calculating includes: excluding the plurality of networked sensors from coordinates in avoidance areas in the facility. Implementations of the described techniques may include hardware, a method or process, or computer software on a computer-accessible medium.

One general aspect includes a system for placement and monitoring of a plurality of networked sensors in a facility that transports materials across a distance, the system including: a plurality of networked sensors configured to detect one or more gaseous plumes resulting from leaks in the facility; a data store configured to store a digital representation of the facility, where the digital representation includes a plurality of components that transport the materials across the distance and a plurality of zones spread across the facility; and an emissions monitoring apparatus including a processor and a memory storing computer-executable instructions that, when executed by the processor, cause the system to perform steps including: The system also includes algorithmically calculating, by the processor, an optimal placement of a plurality of networked sensors in the digital representation of the facility to detect a gaseous plume resulting from a leak, where the optimal placement includes at least a first coordinate, a second coordinate, and a third coordinate. The system also includes providing instructions, by the emissions monitoring apparatus, to affix a plurality of networked sensors at specific coordinates in the facility, where the instructions indicate a first networked sensor is to be affixed at the first coordinate in the facility, a second networked sensor is to be affixed at the second coordinate in the facility, and a third networked sensor is to be affixed at the third coordinate in the facility. The system also includes updating, by the emissions monitoring apparatus, the digital representation of the facility stored in the data store by replacing the first coordinate, the second coordinate, and the third coordinate with actual coordinates calculated by the emissions monitoring apparatus. Other embodiments of this aspect include corresponding computer systems, apparatus, and computer programs recorded on one or more computer storage devices, each configured to perform the actions of the methods.

Implementations may include one or more of the following features. The system as claimed, where the plurality of zones include LDAR zones, and where a first zone of the plurality of zones is assigned a weight score based on at least a quantity of components located in the first zone and gas sensitivity, and where the algorithmically calculating includes: iterating through a plurality of combinations of the first coordinate, the second coordinate, and the third coordinate to identify, using artificial intelligence (AI), an optimization of a cost function based on weight scores assigned to each of the plurality of LDAR zones. The system may also include where the cost function is based on at least a detection zone of each of the first networked sensor, the second networked sensor, and the third networked sensor; and where the optimization also is based on satisfying a pre-defined coverage percentage threshold for one of: individual LDAR zones, all LDAR zones, and geometric sensor location. The system as claimed, where the materials being transported across the distance include chemical materials, and where the data store is a part of the memory of the emissions monitoring apparatus, and where the memory of the emissions monitoring apparatus stores further computer-executable instructions that, when executed by the processor, cause the system to perform steps including: storing, by the processor in the data store, the digital representation of the facility. The system as claimed, where the plurality of networked sensors includes a sensor assembly configured to measure the current meteorological conditions at the facility, and where the first networked sensor includes multiple sensors of more than one type. Implementations of the described techniques may include hardware, a method or process, or computer software on a computer-accessible medium.

One general aspect includes a non-transitory computer-readable medium storing computer-executable instructions that, when executed by a processor, cause a system to detect a gaseous plume resulting from a leak in a facility by performing steps including: storing, in a data store, a digital representation of a facility including a plurality of components that transport chemical materials across a distance, where the digital representation includes a plurality of zones spread across the facility, and where each zone of the plurality of zones is assigned a weight score based on at least a quantity of components located in its zone and gas sensitivity; algorithmically calculating an optimal placement of a plurality of networked sensors in the digital representation of the facility by iterating through a plurality of combinations of coordinates for each of the plurality of networked sensors to identify, using artificial intelligence (ai), an optimization of a cost function based on weight scores assigned to each of the plurality of zones, where the cost function is based on at least a detection zone of each of the plurality of networked sensors, and where the optimization is further based on satisfying a pre-defined coverage percentage threshold for one of: individual zones, all zones, and geometric sensor location. The non-transitory computer-readable medium storing computer-executable instructions also includes providing instructions to affix the plurality of networked sensors at specific coordinates in the facility, where the instructions indicate a first networked sensor is to be affixed at a first coordinate in the facility, a second networked sensor is to be affixed at a second coordinate in the facility, and a third networked sensor is to be affixed at a third coordinate in the facility. Other embodiments of this aspect include corresponding computer systems, apparatus, and computer programs recorded on one or more computer storage devices, each configured to perform the actions of the methods.

Implementations may include one or more of the following features. The non-transitory computer-readable medium as claimed in any one further storing computer-executable instructions that, when executed by the processor, cause the system to perform steps including: after the plurality of networked sensors are affixed in the facility, calculating, by the emissions monitoring apparatus, the actual coordinates of each of the plurality of networked sensors in the facility by triangulating a wireless signal emitted by each of the plurality of networked sensors. The non-transitory computer-readable medium as claimed in any one where the cost function is further based on: a sensor type and sensitivity of each of the first networked sensor, the second networked sensor, and the third networked sensor, where the detection zone of each networked sensor is derived from its sensor type and sensitivity; and a composition of the chemical materials transported across the distance in the facility in the plurality of components. Implementations of the described techniques may include hardware, a method or process, or computer software on a computer-accessible medium.

BRIEF DESCRIPTION OF THE DRAWINGS

The present disclosure is illustrated by way of example and not limited in the accompanying figures in which like reference numerals indicate similar elements and in which.

Figure 1:
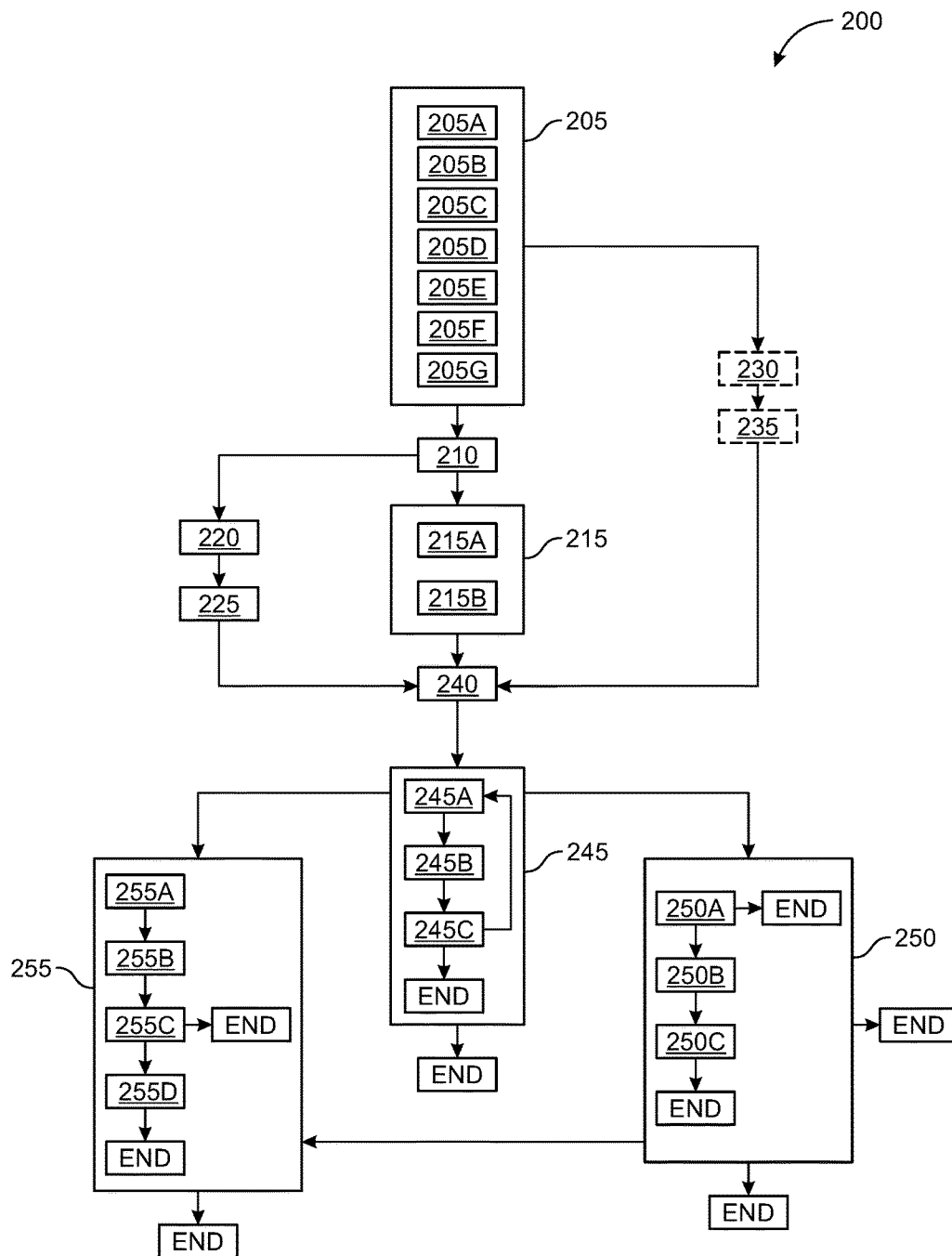
FIG. 1 illustrates a flow chart (with steps and sub-steps) of a sensor placement method which determines where to place sensors within a facility to ensure optimal detection of fugitive emissions within the facility, while minimizing/reducing the number of sensors required to be placed within the facility to accomplish same, in accordance with various aspects of the disclosure.

In the following description of various illustrative embodiments, reference is made to the accompanying drawings, which form a part hereof, and in which is shown, by way of illustration, various embodiments in which aspects of the disclosure may be practiced. It is to be understood that other embodiments may be utilized and structural and functional modifications may be made, without departing from the scope of the present disclosure. It is noted that various connections between elements are discussed in the following description. It is noted that these connections are general and, unless specified otherwise, may be direct or indirect, wired or wireless, and that the specification is not intended to be limiting in this respect.

DETAILED DESCRIPTION

This disclosure describes numerous embodiments involving a facility susceptible to fugitive emissions. One embodiment involves a system and method of locating fugitive emissions. Another embodiment involves a system and method of placing sensors within the facility. Other embodiments are also disclosed herein involving derivations and combinations of the various method steps and system components disclosed herein. While the disclosure may be susceptible to embodiment in different forms, there is shown in the drawings, and herein will be described in detail, specific embodiments with the understanding that the present disclosure is to be considered an exemplification of the principles of the disclosure and is not intended to limit the disclosure to that as illustrated and described herein. Therefore, unless otherwise noted, features disclosed herein may be combined to form additional combinations that were not otherwise shown for purposes of brevity. It will be further appreciated that in some embodiments, one or more elements illustrated by way of example in a drawing(s) may be eliminated and/or substituted with alternative elements within the scope of the disclosure.

In one embodiment involving a method of placing sensors within a facility, a gas sensor network system provides continuous monitoring of fugitive emissions of VOC compounds in chemical plants and facilities. In an embodiment, the present disclosure provides a sensor placement method which determines where to place sensors within a facility while minimizing/reducing the number(s) of sensors required to be placed within the facility to accomplish same. The sensor placement method includes obtaining plant layout, gas composition, meteorological seasonal patterns and/or other types of information regarding a facility where the sensor system is to be implemented, determining the types of gas and ancillary sensors needed, and generating the minimum detection distances required based on the sensitivities of the sensors to the gas compounds involved, and then calculating the minimal number of sensors required for each sensor type with optimized sensor locations to ensure best coverage of potentially leaking components within the facility.

In a further embodiment, the present disclosure provides a sensor placement method which determines where to place sensors within a facility to best ensure detection of fugitive emissions within the facility, while minimizing/reducing the number of sensors required to be placed within the facility to accomplish same. The sensor placement method includes the following steps: (a) obtaining various types of information regarding a facility where a sensor network-based emissions monitoring system is to be implemented; (b) determining the type of gas sensors needed in order to accurately sense/detect fugitive emissions within the facility; (c) generating one or more simulated LDAR zones which represent the general areas/locations within the facility that are subject to LDAR work practices in view of EPA Method 21; (d) determining a minimum detection distance from the leak to the sensor; (e) incorporating the minimum detection distance into detection zones associated with a particular sensor location; (f) identifying a pre-defined coverage percentage threshold of the LDAR zones; and (g) generating a geometric sensor location optimization such that the pre-defined coverage percentage threshold is met/achieved.

Remote detecting of gas plumes created by component leaks provides an innovative way of monitoring fugitive emissions of VOC compounds—it is faster and more effective in detecting large leaks and controlling total emissions from the plants. Thus, efforts have been put forth to develop sensor network-based emissions monitoring systems that are configured to detect plumes of VOCs, or other gases of interest, within the boundaries of a facility. The monitoring system generally includes the placement of sensor nodes throughout the facility, meteorological stations, and a data analytics and visualization platform. The sensors are installed in fixed locations throughout the process unit and wirelessly communicate with a central data platform, which estimates leak locations by analyzing data with site-specific algorithms. With proper sensor placement, a system can quick detect VOC leaks as low as a few grams per hour as far as 60 ft away from the leak. As a part of a layered monitoring framework, optical gas imaging and other technologies are deployed to pinpoint and assess the actual emission source after notification and/or in supplementary form. Further developments include the ability to send alerts and notifications to designated personnel when anomalous emissions were detected, and probable source location was identified.

A factor in the success and viability of the implementation of sensor network-based emissions monitoring systems relies on the ability of the systems to quickly and/or reliably locate leaks within the facility. Existing practices rely heavily on manual work flows and have significant delays in detecting and locating emissions.

Figure 4:
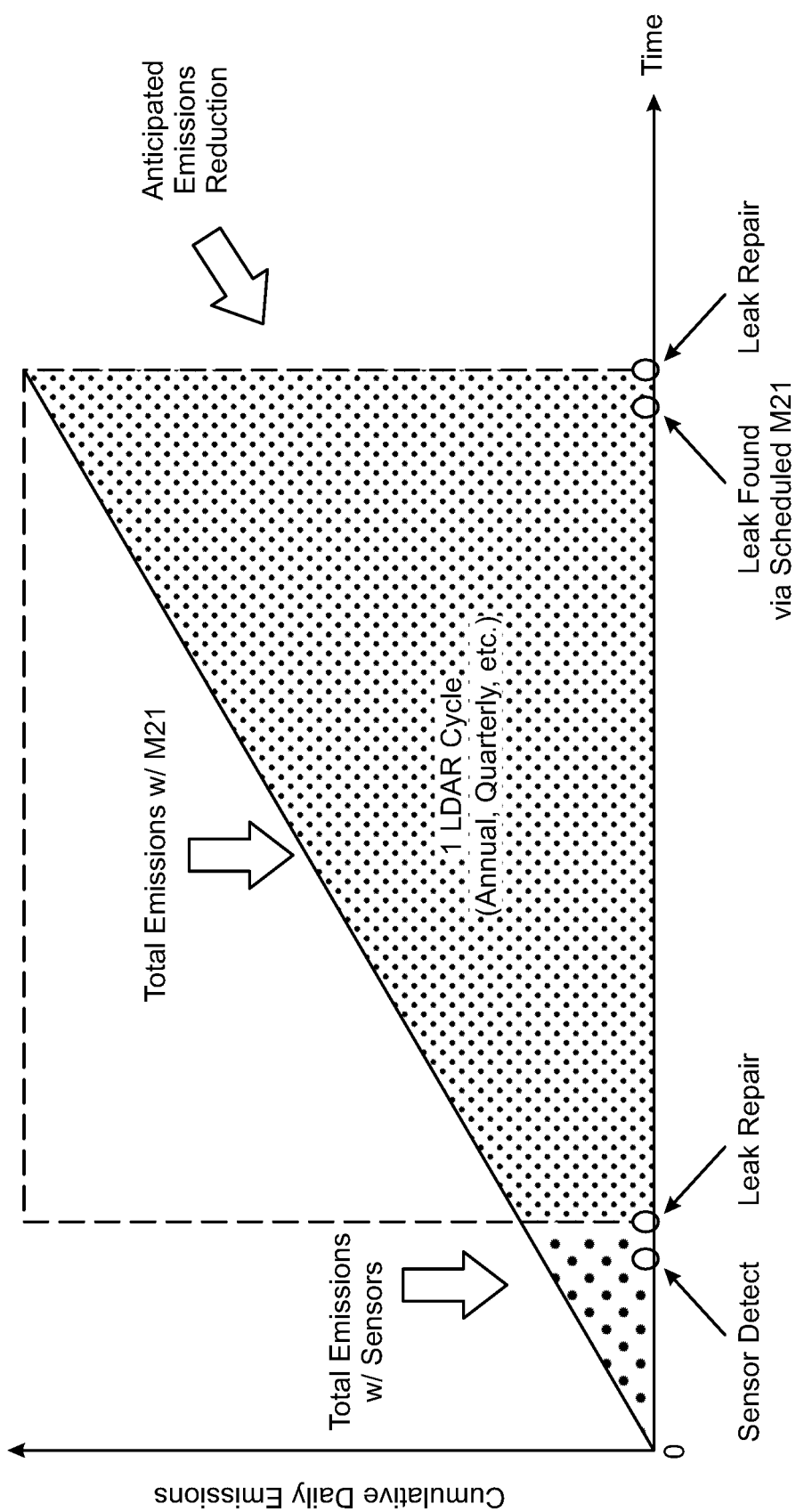
FIG. 4 is a chart illustrating reductions in total emissions by detecting large leaks earlier, in accordance with various aspects of the disclosure.

From the shared perspective of industrial facilities, workers, regulators, and nearby communities, cost-effective detection and management of fugitive emissions (leaks) is a mutually beneficial concept. At least one benefit of one or more embodiments disclosed herein is that unanticipated emissions requiring mitigation may be detected and repaired in a timely manner. As a result, one or more benefits may be realized, including but not limited to: (a) reduced emissions of air pollutants as illustrated in FIG. 4; (b) safer working environments; (c) reduced resource waste through more efficient work practices and by minimizing product loss; and (d) improved emissions inventory knowledge and communications with regulators and communities. In addition, one or more embodiments disclosed herein describe improvements in methods for determining where to place sensors within a facility to better ensure detection of fugitive emissions within the facility, while minimizing (i.e., reducing) the number of sensors required to be placed within the facility to accomplish same.

Referring to FIG. 1, the present disclosure provides an embodiment of a sensor placement method 200 which determines where to place sensors within a facility to best ensure detection of fugitive emissions within the facility, while minimizing/reducing the number of sensors required to be placed within the facility to accomplish same. The sensor placement method 200 is illustrated in FIG. 1.

A step 205 of the sensor placement method 200 is to preferably obtain various types of information regarding a facility where a sensor network-based emissions monitoring system is to be implemented. Step 205 may include a plurality of sub-steps 205A, 205B and 205C. Step 205 may further include a plurality of additional sub-steps 205D, 205E, 205F and 205G.

Sub-step 205A is a step of obtaining information regarding the layout of the facility itself. Information regarding the layout of the facility may include, but is not limited to: two-dimensional drawings and/or three-dimensional CAD models showing the structures within the overall facility; the general width/length/height of such structures; information about the structures themselves, e.g., what they are, what they do, etc.; and information about the physical relationship between the structures, e.g., how closely they are positioned to one another, how large/small they are relative to one another, how tall they are relative to one another, etc. While a three-dimensional model is suitable, the foregoing information (or part of it) may also be provided in unprocessed 3D point cloud or mesh files which are taken by a 3D laser or camera scanning survey. A distribution of platforms with LDAR components may be captured through an initial walkthrough, manual measurements, or other methods. CAD drawings from the plant may often be inhomogeneous, such that components are not all of the same degree or dimensions.

Sub-step 205B is a step of obtaining information regarding the process stream composition of the facility. Information regarding the process stream composition of the facility may include, but is not limited to: the types of liquids/gases being processed at various areas/elevations of the facility; and the types of fugitive emissions that may emanate from the various components within the facility if a leak occurs.

Sub-step 205C is a step of obtaining information regarding LDAR regulations that the facility is subject to. Information regarding LDAR regulations that the facility is subject to may include, but is not limited to: regulations issued by the federal government; regulations issued by the state government; regulations issued by the county government; and regulations issued by the city government. The information obtained in sub-step 205C may be based, in whole or in part, on the information obtained in sub-step 205D (as described below). The local regulations may depend on the type of facility and chemicals involved (stream composition from sub-step 205B) and provide required minimal leak size definition (in g/hour) per chemical type and/or per component type that area detection system have to detect within a reasonable time period.

If included, sub-step 205D obtains information regarding the physical location of the facility. Information regarding the physical location of the facility may include, but is not limited to: the post-office address of the facility; the GPS coordinates of the facility; and the elevation of the facility.

Another sub-step 205E that can be included is a step of obtaining information regarding the historical meteorological data at a location as proximate to the location of the facility as possible. Information regarding the historical meteorological data (e.g., seasonal weather patterns) may include, but is not limited to: temperature data; humidity data; and wind speed and direction data. The information obtained in sub-step 205E may be based, in whole or in part, on the information obtained in sub-step 205D. The information in sub-step 205E can be used to create one or more representative wind sets to be used for detection distance estimates.

Sub-step 205F can also be included and is a step of obtaining information regarding the historical leak data at the facility. Information regarding the historical leak data may include, but is not limited to: the number of LDAR components; physical location information of individual LDAR component within the facility; and historical LDAR leaks and emissions data for the facility, which data may aid in identifying historical patterns of failure of certain equipment and, thus, may aid in sensor placement (i.e., it may be useful to place one or more sensors close to such equipment).

Optional sub-step 205G is a step of conducting an on-site survey of the facility in order to identify other pertinent information regarding the facility. The survey may include audio-video observations, local wind measurements and background gas measurements using appropriate portable measuring instruments. The other pertinent information may include, but is not limited to: identifying areas close to authorized leaks/emissions; identifying steam reliefs/leaks and high temperature areas; identifying ongoing leaks (which, if identified, can be immediately reported to the facility); identifying delay-of-repair (DOR) leaks; the status of repairs; and identifying information regarding structures/maintenance activities occurring in the facility or close proximity to, but outside of, the facilities boundaries.

In step 210 the type of gas sensors (e.g., appropriate sensor technology) needed in order to accurately sense/detect fugitive emissions within the facility is determined and can be based on stream composition information (e.g., chemicals information) from sub-step 205B. Gas sensors of different types may not have the same sensitivities to different gas species. For example, a catalytic bead sensor may be twice as sensitive to methane and 30% more sensitive to propane compared to pentane. The cross-sensitivities of the sensor are therefore 200% for methane, and 130% for propane upon a pentane calibration. Determination of the type of sensors needed is based on one or more of at least the following: sensitivity of the sensor to the gases present in process streams in substantial or detectable amounts; the criticality of detection due to toxicity; and/or other safety related or other gas type related issues. For complex gas streams or gas mixtures, a gas cross-sensitivity factor may be calculated based on a library of cross-sensitivity factors or cross-sensitivities for different chemicals, as illustrated in the formula below:

$$f_4(X_1, F_1, X_2, F_2, X_3, F_3, \ldots) = \frac{1}{X_1 F_1 + X_2 F_2 * + X_3 F_3 + \ldots}$$

Alternatively, the cross-sensitivity factor may be based on a library of experimental measurements for typical streams (e.g., crude, fuel gas, etc.).

In step 215 one or more simulated LDAR zones are generated and the LDAR zones represent the general areas/locations within the facility that are subject to LDAR work practices in view of EPA Method 21. An example of step 215 is illustrated in FIGS. 3A-3D. The simulated zones can be three-dimensional zones, but may also be two-dimensional zones, or points (e.g., if the facility has specific known location/elevation of each component within the facility that is subject to LDAR testing), and/or a combination of one or more of points, two-dimensional zones and three-dimensional zones. The three-dimensional LDAR zones may be in any three-dimensional form but are preferably generated in simple rectangular prism (or cylinder) shape as such shapes are easier to manage mathematically. The two-dimensional LDAR zones may be in any two-dimensional form, but are preferably generated in simple rectangular or circular shape, as illustrated by the gray boxes and circles in FIGS. 3A-3D, which are easier to work mathematically. In should be noted that the three-dimensional LDAR zones generated in step 215 are not necessarily generated based on substantially solid structures. The LDAR zones generated by step 215 may be generated based, in whole or in part, on the information obtained in, or the determinations made in, one or both of steps 205 (including, for example, sub-steps 205A, 205B, 205C and 205F) and 210. Step 215 may include a one or more of sub-steps 215A and 215B. LDAR zones may be generated from CAD drawings, historical leak analysis, one or more actual walkthroughs. The graphical representation of the LDAR zones may include elevation, number of LDAR components (represented by z-thickness of a LDAR zone), accessibility factor of LDAR zone, noise/sensitivity factor (e.g., from steam and/or heat).

In sub-step 215A a weight factor is assigned to each of the simulated LDAR zones. The weight factors may incorporate the number of LDAR components in the zone, leak probability by age/component type, historical patterns of failure, and criticality of detection, and will be assigned based, in whole or in part, on the information obtained in one or more of sub-steps 205A, 205B, 205C, 205F, and 205G. As can be appreciated, sub-step 215A may not always be practical as not all facilities currently have geolocation data for individual LDAR components or enough historical leak data to assign reliable leak probability. In one example, a weight factor may be assigned to an individual leak zone. The weight factors may be used to skew optimization algorithm to cover "potential leak heavier" zones but may also be part of an acceptance criteria for a pre-defined coverage percentage threshold, as discussed herein. In one example, if a potential leak zone has a weight score more than 5 (e.g., on a 0-10 scale) then it has to be covered 100%, while if the weight score is less than 5 but more than 3, it may be covered 95%, and if it is less than 3, then it may be covered 90%.

Sub-step 215B confirms the accuracy of the simulated LDAR zones and, if assigned, the legitimacy of weight factors with personnel from the facility and, if necessary, based on feedback from the personnel from the facility, modifying the simulated LDAR zones. Thus, sub-step 215B beneficially allows for enhanced LDAR zones.

Step 220 determines a minimum detection distance, preferably a lateral detection distance, from the leak to the sensor depending on leak-to-sensor elevation difference and the sensitivity threshold of the sensor(s) identified in step 210. The minimum detection signal distance can be estimated by utilizing a gas dispersion model or an empirical equation based on the data from other similar facilities or preliminary plant survey with portable gas instrument (e.g., sub-step 205G) to locate/quantify background leaks and representative wind set from sub-step 205E. The dispersion model or empirical equation takes into account information obtained in, or determined by, in whole or in part, sub-step 205A (e.g., elevation), sub-step 205C (e.g., minimal leak size definition), sub-step 205E (e.g., wind data), sub-step 205G (e.g., steam relief and high temperature areas), and step 210 (e.g., various gases cross-sensitivity factors). As can be appreciated, the model used in step 220 may be modified in substantially real-time if updated information associated with sub-step 205E is provided. In one example, algorithmic calculating may be performed using one or more equations related to maximal detection distance (D_max), as explained below with respect to FIG. 3B, FIG. 3C, and FIG. 3D.

Step 225 incorporates minimum detection distance data from step 220 into detection zones associated with a particular sensor location. Typical facilities, such as chemical plants, have multiple elevations (platforms, floors, etc.), and sensors may detect leaks not only from the elevation where it is located, but also from adjacent (upper/lower) elevations. Step 225 can be performed in several ways. In one embodiment, when LDAR zones are three dimensional, the minimum detection distance as a function of leak-to-sensor elevation difference is converted into a minimum detection signal volume of the sensors identified in step 210. The minimum detection volume is defined as if the smallest leak (as defined by local regulations in sub-step 205C) occurs within the detection volume of the sensor, the leak can reliably be detected by the particular gas sensor identified in step 210. Outside the detection volume, the smallest leak is not likely to be detected. The sensitivity threshold may vary at different locations and elevations within the facility because of different gases together with gas noise and background variations due to local temperature, humidity, steam presence, background leaks. As a result, calculated detection volume may be a function of sensor location and elevation. In another embodiment, when LDAR zones comprise a set of two dimensional shapes sorted by elevation, each sensor will have two or more (or in some examples, three or more) minimum detection distances or detection radii attached to it: detection distance (1) for the leaks found on the same elevation as the sensor, and more additional detection distances (2, 3, . . . ) for the leaks at different elevation with respect to the sensor. For example, for the sensor installed on the $4^{th}$ level/floor, the detection distance (1) is defined for the potential leaks present on the same $4^{th}$ level/floor, the detection distance (2) is defined for the potential leaks present on the $3^{rd}$ level/floor, and the detection distance (3) is defined for the potential leaks present on the $5^{th}$ level/floor. For facilities where floors are not readily definable, elevation ranges can be substituted for floors. In addition, as can be appreciated, two dimensional zones can be converted into three dimensional zones. In summary, detection zones can be three dimensional volumes (three-dimensional LDAR zones) or a set of detection areas corresponding to different potential sensor-to-leak elevations.

Step 230 generates one or more three-dimensional simulated zones which represent the size/shape/location/elevation of one or more generally solid structures, e.g., buildings, vessels, columns, towers, pools, fin-fans, etc., within the facility. The three-dimensional zones may be in any three-dimensional form, but are preferably generated in simple rectangular prism (or cylindrical) shape. The three-dimensional zones generated by step 230 may be generated based on the information obtained in sub-step 205A. It should be noted that the minimum detection distance in step 220 may be determined without incorporating any possible wind obstructions due to the presence of the three-dimensional zones generated in the sixth step 230. In addition, step 235 determines allowance and avoidance areas, e.g., locations/areas where sensors can be placed or should not be placed within the facility. Some examples of allowance areas include various high elevation platforms or battery limits (namely, a physical boundary, such as, for example, a flange on a pipe), defined between two areas of responsibility), identified in step 205A, when the sensor cannot be placed outside the platform or battery limit. Some examples of avoidance areas include open or walking areas, wind shade zones, three-dimensional zones from step 230, and the places where steam relief and high temperature areas have been identified (by sub-step 205G). Wind shade zones are defined as, for example, areas/volumes that are blocked or substantially immune to wind due to the presence of structures within the facility. The wind shade zones can be estimated by utilizing computational fluid dynamics (CFD) calculations and/or an empirical equation or with the use of sensors if sufficient sensors can be appropriately positioned.

The CFD model or empirical equation incorporates information obtained in, or determined by, in whole or in part, sub-step 205A (e.g., elevation), sub-step 205E (e.g., wind data) and step 230 (e.g., 3D dimensional zones). The wind shade zones can be determined with or without gas dispersion modeling.

Step 230 and step 235 in FIG. 1 are in dashed line to denote that, in some examples, they are optional. In one example, step 205 comprises steps to obtain various types of information about a facility where a sensor network-based emissions monitoring system is to be implemented. And then, without performing step 230 or step 235, step 240 may be performed to identify a pre-defined coverage percentage threshold of zones in the facility. One or more steps of the aforementioned method may not be required, one or more steps may be performed in a different order than as described, and one or more steps may be formed substantially contemporaneously.

Step 240 identifies a pre-defined coverage percentage threshold of the LDAR zones identified in step 215. The pre-defined coverage percentage threshold would be dictated by one or more of those who operate/manage the facility and various rules/regulations. The default coverage for LDAR regulated facilities may be 100%, in some examples, however, other chemical facilities may not require a full coverage or can make economy-driven decisions of practical coverage based on criticality or remoteness of some components. In this case, the algorithm will optimize sensor placement to achieve the predefined practical coverage and clearly identify and report non-covered areas to the facility. It should be noted that some remote or isolated LDAR components may be manually unmarked as "non-covered" in step 215 such that the algorithm does not take them into account as a part of the optimized sensor placement. However, it would be preferred that all LDAR zones be noted in step 215 and that the algorithm ultimately "decide" on which areas should be "non-covered". Further, a combination of both could be utilized in practice. The pre-defined coverage percentage threshold could be a specific percentage (e.g., 80%, 90%, or other percentage), or the pre-defined coverage percentage threshold could be in a specific percentage range (e.g., 80-85%, 90-89%, or other range). In some examples, a pre-defined coverage limit may be assigned to individual zones.

Step 245 of the sensor placement method 200 is to preferably generate a geometric sensor location optimization, which identifies the exact location/elevation where each sensor should be placed within the facility such that the pre-defined coverage percentage threshold defined in step 240 is met/achieved. Step 245 may include one or more of a plurality of sub-steps 245A, 245B and 245C.

Sub-step 245A identifies a number of sensors that should be placed within the facility. This sub-step 245A can be performed by a simple ratio of a total area/volume of LDAR zones on the floor by minimum detection area/volume, an optimization algorithm that takes into account the results of step 215, sub-step 215B (if utilized), and step 225, a semi-manual optimization algorithm, or an entirely manual process (no algorithm is used, but rather an educated guess is used). Naturally, if sensors are sufficiently inexpensive then additional sensors can be added but because of maintenance needs it may be desirable to limit the number of sensors to an amount that roughly corresponds to the number determined in step 245A.

Sub-step 245B optimizes sensor location by running an algorithm which identifies the exact location/elevation where each sensor should be placed within the facility and which would identify a coverage percentage of the LDAR zones identified in step 215. This algorithm preferably incorporates the information from one or more of the following: step 215 (LDAR zones), sub-step 215B (weight factors) (if provided), step 225 (detection volume/area), step 235 (allowance/avoidance areas) (if provided), and sub-step 245A (number of sensors). The optimization algorithm calculates a matrix of volumetric/area overlaps between all LDAR zones and all detection zones associated with each sensor and minimizes/reduces total uncovered volume/area of all LDAR zones, while sensor location coordinates vary within allowance areas (elevated platforms, etc.) and outside avoidance areas (steam areas, structures, etc.). In one example, the aforementioned algorithm may maximize overlap between potential leak zones and detection zones, while minimizing the number of sensors.

Sub-step 245C compares the coverage percentage calculated in sub-step 245B with the pre-defined coverage percentage threshold identified in step 240. If the coverage percentage calculated in sub-step 245B is in accordance with the pre-defined coverage percentage threshold identified in step 240, the sensor placement method 200 may optionally be completed such that sensors can then be placed within the facility at the exact location/elevation identified in sub-step 245B. FIGS. 3A-3D illustrate, in two-dimensional form, the optimized number and location of sensors within the facility which provides optimized locations of detection zones of the sensors across the LDAR zones (where the black dot indicates the location of the sensor and the circle surrounding the black dot indicates the detection zone of each sensor). If, however, the coverage percentage identified in sub-step 245B is greater or less than the pre-defined coverage percentage threshold identified in step 240, then step 245 can be repeated with some modifications as compared to the previous time that step 245 was performed. More specifically, if the coverage percentage identified in sub-step 245B is greater than the pre-defined coverage percentage threshold identified in step 240, then step 245 is repeated by modifying sub-step 245A to identify a smaller number of sensors, e.g., one lower than that previously identified, and then repeating sub-steps 245B and 245C. If the coverage percentage identified in sub-step 245B is less than the pre-defined coverage percentage threshold identified in step 240, then step 245 is repeated by modifying sub-step 245A to identify a larger number of sensors, e.g., one more than that previously identified, and then repeating sub-steps 245B and 245C. This iterative process helps ensure the sensor placement is close to the preferred optimum case. In one example, one aspect of the optimization that may occur is an algorithm/methodology to minimize/eliminate positioning of sensors on top of each other. Optimal placement of sensors is achieved by distributing and orienting sensors to maximize coverage and perspective to detect and better pin-point a leak.

As noted, the sensor placement method 200 may optionally be finalized upon step 245 being completed. However, the sensor placement method 200 may also include step 250 and/or step 255 to further validate the exact location/elevation where each sensor should be placed within the facility.

Step 250 validates the exact location/elevation where each sensor should be placed within the facility by ensuring that it is feasible to place a sensor at the identified location/elevation. Step 250 may include a plurality of sub-steps 250A, 250B and 250C.

Sub-step 250A compares the location/elevation of each sensor as determined by step 245 with the actual physical layout of the facility (this could be done based on one or more of: the information obtained in sub-step 205A, a visit to the facility, feedback from the personnel from the facility) to determine whether it is feasible to place a sensor at the identified location/elevation. If each sensor can be positioned/mounted at their respective locations/elevations, then the sensor placement method 200 may again be optionally finalized upon sub-step 250A being completed. However, if one or more of the sensors cannot feasibly be positioned/mounted at their respective locations/elevations, then sub-steps 250B and 250C can be performed.

Sub-step 250B identifies the closest feasible location/elevation where the sensor(s) could be positioned/mounted and recording the location/elevation thereof. This can be done by comparing the computed location with physical structures so as to determine an alternative location that is close to the computed location.

Sub-step 250C reruns sub-steps 245B and 245C, but with a modified version of the algorithm performed in sub-step 245B. The modified version of the algorithm may include inputting the new location/elevations of the respective sensors in order to ensure that the coverage percentage meets the pre-defined coverage percentage threshold of step 240. It should be noted that if the new location/elevation is within a predetermined range of the original location/elevation (e.g., within five feet), then the sensor placement method 200 may again be optionally finalized upon sub-step 250B being completed (as such minor changes would likely not drastically change the overall coverage percentage).

Step 255 validates the exact location/elevation where each sensor should be placed within the facility based on 3D modeling. Step 255 may occur after the completion of step 245 or after the completion of step 250. Step 255 may include a plurality of sub-steps 255A, 255B, 255C and 255D.

Sub-step 255A identifies one or more representative sets of leaks (e.g., 10-100—individually). The leaks in each set would have their individual leak sizes (e.g., in g/hour) set to the minimal leak size definition for the particular LDAR zones from step 215 and for the relevant local regulations from sub-step 205C. The leak locations identified in sub-step 255A may include, but are not limited to, a set of random locations within the LDAR zones from step 215, a set of potentially difficult to detect areas (towers, open or structurally highly packed areas within the vicinity of large vessels, etc.), or a set of critical to detect areas.

Sub-step 255B conducts a set of wind and gas dispersion simulations using the representative leak sets identified in sub-step 255A and the representative wind sets identified in sub-step 205E. The modeling can be a set of transient CFD simulations (wind/turbulences and species transport) for each leak location, a time-set of steady state CFD wind maps (for each wind speed/direction in representative wind-set) with preferably transient (in some cases steady state) gas dispersion simulations for the time-set of wind maps for each leak location. The result of the simulations is a set of multiple gas concentration (e.g., in parts per billion) trends vs. time for each sensor location.

Sub-step 255C compares the highest detects from sub-step 255B to the practical sensitivity of the sensor(s) identified in step 210 to determine if the leak is detectable or not. A set of simulated leaks that pass the detection criteria preferably should agree with the predefined sensor coverage from step 240 or any additional criticality of detection requirements. If the set of simulated leaks passes the detection criteria (e.g., it is in accordance with the pre-defined coverage percentage threshold from step 240), then the sensor placement method 200 may again be optionally finalized upon sub-step 255C being completed. However, if the set of simulated leaks does not pass the detection criteria, then sub-step 255D may be performed.

Sub-step 255D reruns step 245 by modifying the number of sensors as a part of sub-step 245A and/or by using a modified version of the algorithm performed in sub-step 245B. The modified version of the algorithm would include inputting the new location/elevations of the respective sensors in order to ensure that the coverage percentage meets the pre-defined coverage percentage threshold of step 240.

While particular embodiments are illustrated in and described with respect to the drawings, it is envisioned that those skilled in the art after review of the entirety disclosed herein may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure and the appended claims. Further, the foregoing descriptions describe methods that recite the performance of a number of steps. Unless stated to the contrary, one or more steps within a method may not be required, one or more steps may be performed in a different order than as described, and one or more steps may be formed substantially contemporaneously. It is further understood that the actions identified in steps 205, 210, 215, 220, 225, 230, 235, 240, 245 (including any one or more of their respective sub-steps) are all preferably performed by, or under the direction of, a single entity.

Figure 2A:
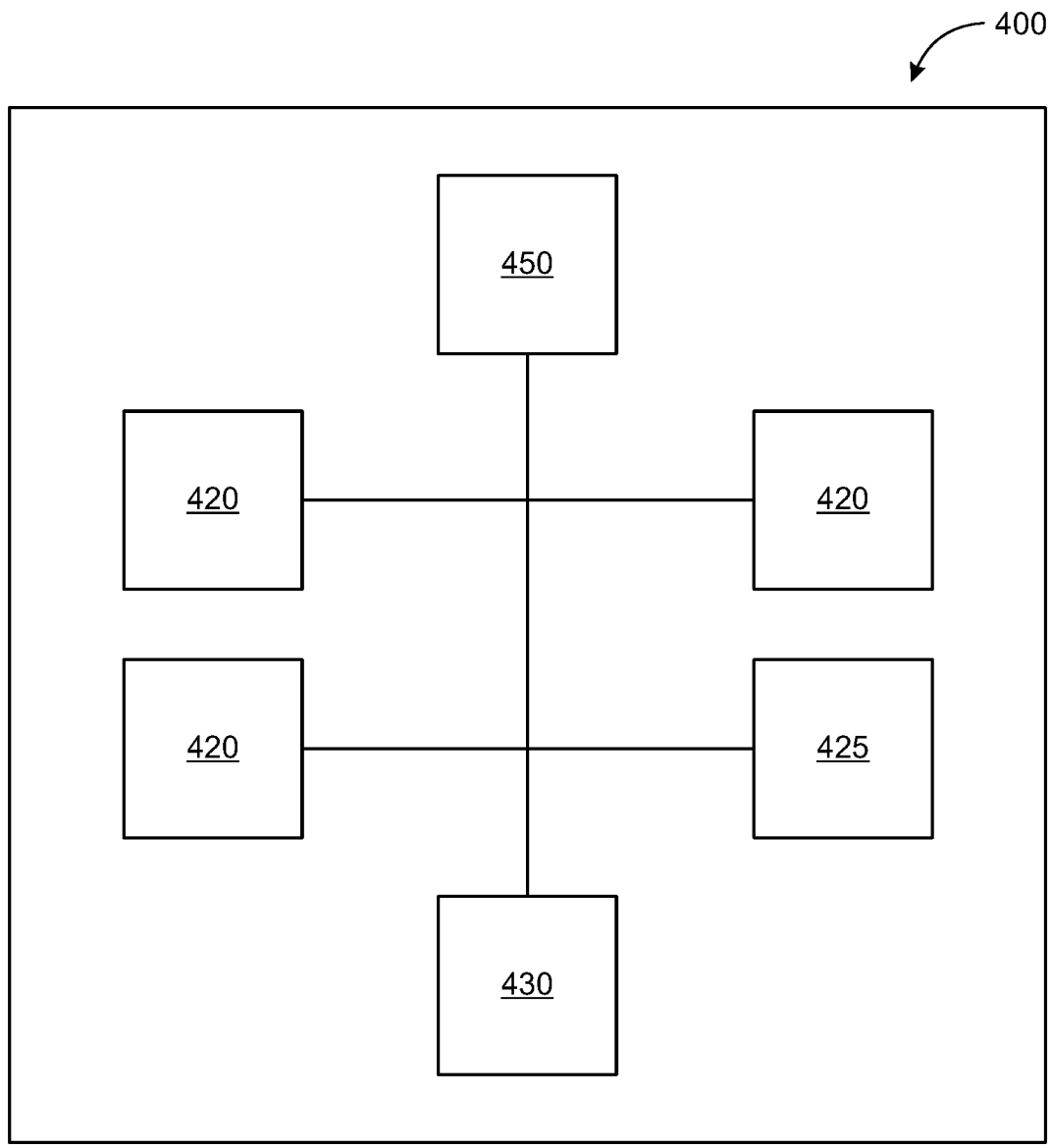
FIG. 2A and FIG. 2B provide a schematic illustration of a sensor network-based emissions monitoring system which is used, in whole or in part, to perform the method illustrated in FIG. 1, in accordance with various aspects of the disclosure.

Referring to FIG. 2A, the sensor network-based emissions monitoring system 400, which is schematically depicted in FIG. 2A, may include a plurality of sensors 420 positioned at desired locations throughout the facility. In an embodiment, the specific location/orientation of each sensor 420 is readily known/ascertainable. The sensors 420 are preferably in communication with a control head 450. In one example, the control head 450 may comprise a processor and memory located in the facility. In another example, one or more processors may be remotely located and in communication with the control head 450 via a (wireless or wired) data link. In yet another example, one or more memories may be remotely located and in communication with the control head 450 via a (wireless or wired) data link. In another example, the control head 450 may comprise a controller that interfaces with one or more mechanical, electro-mechanical, or other types of components of the industrial facility to control their behavior.

If desired, one or more additional sensors 425 may also be provided. In one embodiment, the sensors 420 and sensors 425 are different sensors, either with different sensitivities generally or with different performance under certain conditions. Certain sensors, for example, might be more sensitive to certain chemicals than other chemicals. By having a mix of sensors, a more complete sensor system can be provided. Sensors other than sensors 420, 425 could also be provided. The sensors 420, 425 can be configured to provide feedback to the control head 450 generally continuously, on predetermined intervals, or when predetermined events take place (or some or all). The control head 450 can also be provided environmental information such as temperature, wind speed, humidity, pressure, etc.

The control head 450 may, in some examples, be programmed with artificial intelligence 430. The artificial intelligence 430 may be executed on one or more artificial neural networks in accordance with various aspects of the disclosure described herein. By way of background overview, a framework for machine learning algorithm may involve a combination of one or more components, sometimes three components: (1) representation, (2) evaluation, and (3) optimization components. Representation components refer to computing units that perform steps to represent knowledge in different ways, including but not limited to as one or more decision trees, sets of rules, instances, graphical models, neural networks, support vector machines, model ensembles, and/or others. Evaluation components refer to computing units that perform steps to represent the way hypotheses (e.g., candidate programs) are evaluated, including but not limited to as accuracy, prediction and recall, squared error, likelihood, posterior probability, cost, margin, entropy k-L divergence, and/or others. Optimization components refer to computing units that perform steps that generate candidate programs in different ways, including but not limited to combinatorial optimization, convex optimization, constrained optimization, and/or others. In some embodiments, other components and/or sub-components of the aforementioned components may be present in the system to further enhance and supplement the aforementioned machine learning functionality.

Machine learning algorithms sometimes rely on unique computing system structures. Machine learning algorithms may leverage neural networks, which are systems that approximate biological neural networks (e.g., the human brain). Such structures, while significantly more complex than conventional computer systems, are beneficial in implementing machine learning. For example, an artificial neural network may be comprised of a large set of nodes which, like neurons in the brain, may be dynamically configured to effectuate learning and decision-making.

Machine learning tasks are sometimes broadly categorized as either unsupervised learning or supervised learning. In unsupervised learning, a machine learning algorithm is left to generate any output (e.g., to label as desired) without feedback. The machine learning algorithm may teach itself (e.g., observe past output), but otherwise operates without (or mostly without) feedback from, for example, a human administrator. Meanwhile, in supervised learning, a machine learning algorithm is provided feedback on its output. Feedback may be provided in a variety of ways, including via active learning, semi-supervised learning, and/or reinforcement learning. In active learning, a machine learning algorithm is allowed to query answers from an administrator. In semi-supervised learning, a machine learning algorithm is provided a set of example labels along with unlabeled data. In reinforcement learning, a machine learning algorithm is rewarded for correct labels, allowing it to iteratively observe conditions until rewards are consistently earned.

One theory underlying supervised learning is inductive learning. In inductive learning, a data representation is provided as input samples data (x) and output samples of the function (f(x)). The goal of inductive learning is to learn a good approximation for the function for new data (x), i.e., to estimate the output for new input samples in the future. Inductive learning may be used on functions of various types: (1) classification functions where the function being learned is discrete; (2) regression functions where the function being learned is continuous; and (3) probability estimations where the output of the function is a probability.

In practice, machine learning systems and their underlying components may be tuned by data scientists to perform numerous steps to perfect machine learning systems. The process is sometimes iterative and may entail looping through a series of steps: (1) understanding the domain, prior knowledge, and goals; (2) data integration, selection, cleaning, and pre-processing; (3) learning models; (4) interpreting results; and/or (5) consolidating and deploying discovered knowledge. This may further include conferring with domain experts to refine the goals and make the goals clearer, given the nearly infinite number of variables that can possibly be optimized in the machine learning system. Meanwhile, one or more of data integration, selection, cleaning, and/or pre-processing steps can sometimes be the most time consuming because the old adage, "garbage in, garbage out," also reigns true in machine learning systems.

Once data for machine learning has been created, an optimization process may be used to transform the machine learning model. The optimization process may include (1) training the data to predict an outcome, (2) defining a loss function that serves as an accurate measure to evaluate the machine learning model's performance, (3) minimizing the loss function, such as through a gradient descent algorithm or other algorithms, and/or (4) optimizing a sampling method, such as using a stochastic gradient descent (SGD) method where instead of feeding an entire dataset to the machine learning algorithm for the computation of each step, a subset of data is sampled sequentially.

Figure 2B:
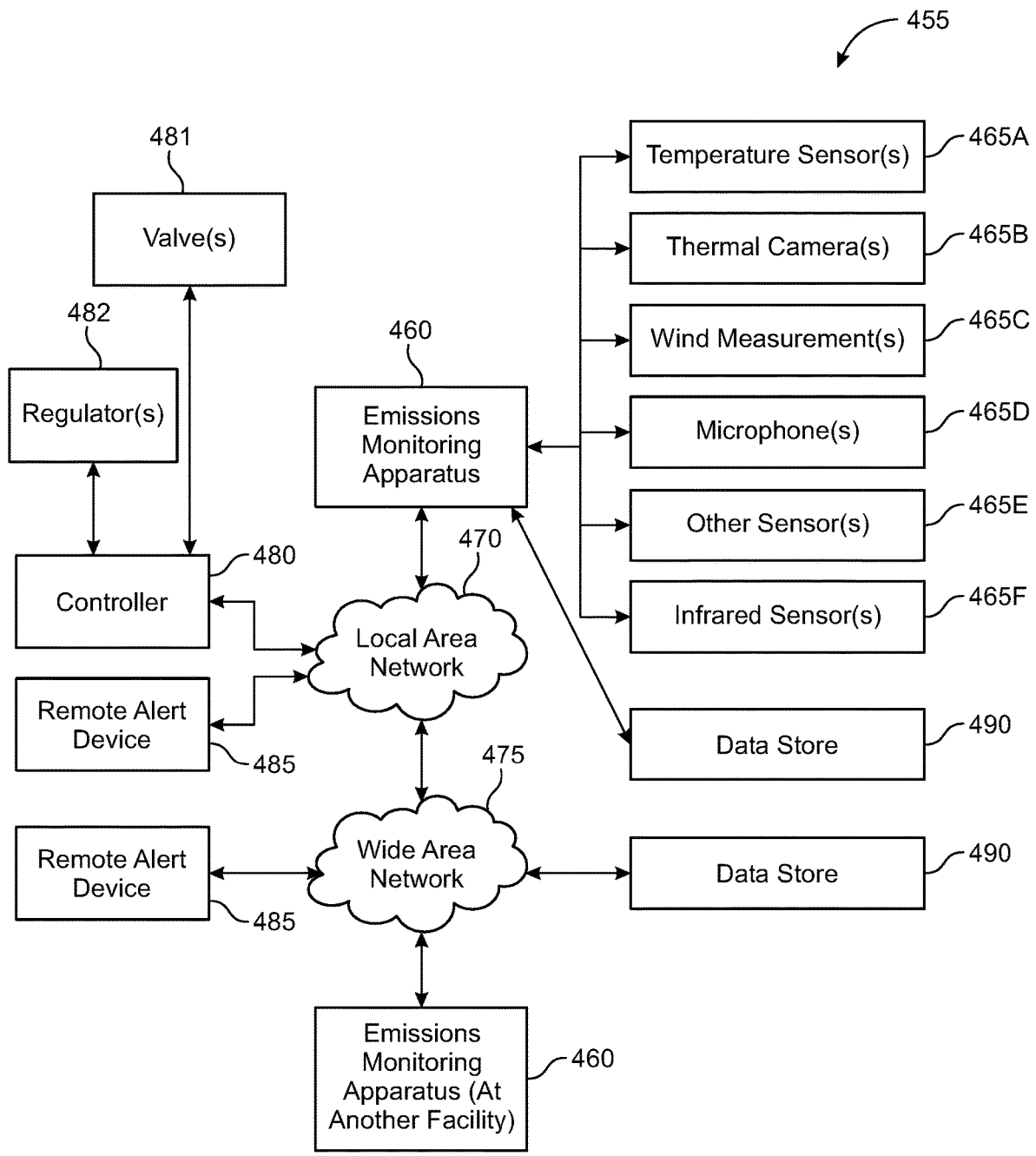

FIG. 2B illustrates a block diagram of another example of a sensor network-based emissions monitoring system 455 which is used, in whole or in part, to perform the methods described herein. While the system 455 of FIG. 2B shares several similar aspects as system 400 in FIG. 2A, the system 455 of FIG. 2B is intended to illustrate alternative variations on system 400 contemplated by the disclosure. The disclosure is not limited to just the combination of elements depicted in FIG. 2A and FIG. 2B; rather, numerous variations of the sensor network-based emissions monitoring system are contemplated by the method steps, apparatus components, system interactions, and other aspects disclosed herein. For example, the emissions monitoring apparatus 460 may be communicatively coupled with one or more sensors, such as a temperature sensor 465A, thermal camera 465B, wind measurement device 465C, one or more microphones 465D, infrared sensor 465F, and/or one or more other sensors 465E. In one example, one transmitter may carry multiple sensors of one or more types. For example, a single sensory assembly may comprise multiple sensors of one or more types. In other example, a networked sensor may comprise multiple sensors of more than one type. The sensors operate to collect measurements in near real-time for input to the emissions monitoring apparatus 460.

The computing system environment 455 of FIG. 2B includes logical block diagrams of numerous platforms and devices that are further elaborated in this disclosure. FIG. 2B is an illustrative emissions monitoring system with one or more processing apparatuses to implement the methods and functions of certain aspects of the present disclosure. The processing apparatuses may include general-purpose microprocessors and/or special-purpose processors designed for particular computing system environments or configurations. For example, the processors may execute computer-executable instructions in the form of software and/or firmware stored in the memory of the platform or device.

Examples of well-known computing systems, environments, and/or configurations that may be suitable for use with the disclosed embodiments include, but are not limited to, personal computers (PCs), server computers, hand-held or laptop devices, smart phones, multiprocessor systems, microprocessor-based systems, programmable consumer electronics, network PCs, minicomputers, mainframe computers, distributed computing environments that include any of the above systems or devices, and the like.

In addition, the platform and/or apparatuses in FIG. 2B may comprise one or more memories, such as any of a variety of computer-readable media. Examples of computer-readable media may include tangible computer memory accessible to an emissions monitoring apparatus 460. The memory may be non-transitory, volatile or nonvolatile, and/or removable and non-removable media implemented in any method or technology for storage of information, such as computer-readable instructions, object code, data structures, database records, program modules, or other data. Examples of computer-readable media may include random access memory (RAM), read only memory (ROM), electronically erasable programmable read only memory (EEPROM), flash memory or other memory technology, compact disk read-only memory (CD-ROM), digital versatile disks (DVD) or other optical disk storage, magnetic cassettes, magnetic tape, magnetic disk storage or other magnetic storage devices, or any other medium that can be used to store the desired information and that can be accessed by emission monitoring apparatus 460. The memories may further include data store 490 in the platform and may further store modules that may include compiled software code that causes the platform, device, and/or overall system to operate in a technologically improved manner as disclosed herein. For example, the data store 490 may store software used by a computing platform, such as operating system, application programs, and/or associated database.

Furthermore, the devices in FIG. 2B may include one or more communication interfaces including, but not limited to, a microphone, keypad, touch screen, and/or stylus through which a user of a computer (e.g., remote device 485) may provide input, and may also include a speaker for providing audio output and a video display device for providing textual, audiovisual and/or graphical output. The communication interfaces may include a network controller for electronically communicating (e.g., wirelessly or wired) over a public network 475 or a private network 470 with one or more other components on the network. The network controller may include electronic hardware for communicating over network protocols, including TCP/IP, UDP, Ethernet, and/or other protocols. In some examples, the emissions monitoring apparatus 460 may be a cloud-based device that operates remote from the facility over a computer network.

Controller 480 may interact with and/or execute commands received from an emissions monitoring apparatus 460. The controller 480 may be communicatively coupled to the emissions monitoring apparatus 460 and configured to actuate one or more tangible components in the facility. For example, the facility may include a valve component 481 that is assembled between a first component and a second component that transports gaseous materials throughout the facility. The controller 480 may actuate the valve component 481 from an open position to a closed position, and vice versa. For example, the components may be transporting gaseous materials across a distance in the facility, and when a leak source is detected originating from the second component that transports gaseous materials throughout the facility, the controller may issue a command to actuate the valve component 481 into a closed position, thus shutting off the flow of gas to the component with the source of the leak. In another example, the controller 480 may be communicatively coupled with a regulator 482 component.

Referring to FIG. 2B, in one example, a remote alert device 485 may comprise a processor, a memory, and/or a communication interfaces. The processor may process and analyze the data stored in the memory. In some embodiments, the memory may store computer-executable instructions that, when executed by the processor, cause a remote alert device 485 to perform one or more of the steps disclosed herein. In some embodiments, the system 455 may generate alerts based on values received through the communications interface. The values may indicate that a dangerous gas leak has been detected in the facility due to anomalous sensor readings, thus causing adjustment of one or more operating parameters of the facility. As explained above, in one example, the remote alert device 485 may display a graphical user interface (GUI) to a user of the device to enable the user to enter desired parameters and/or commands. As a result of adjustment of the operating parameters, the facility may cause adjustments or halting/starting of one or more operations. In an alternative embodiment, the commands may be directly communicated, either wirelessly or in a wired fashion, to physical components at the facility such that the physical components include an interface to receive the commands and execute them.

Although FIG. 2B is not so limited, in some embodiments the remote alert device 485 may include a desktop computer, a smartphone, a wireless device, a tablet computer, a laptop computer, and/or the like. The remote alert device may be physically located locally or remotely, and may be connected by one of communications links.

Although the elements of FIG. 2B are illustrated as logical block diagrams, the disclosure is not so limited. In particular, one or more of the logical boxes in FIG. 2B may be combined into a single logical box or the functionality performed by a single logical box may be divided across multiple existing or new logical boxes. Moreover, some logical boxes that are visually presented as being inside of another logical box may be moved such that they are partially or completely residing outside of that logical box. For example, FIG. 2B contemplates that data store 490 may be stored inside a firewall (e.g., internal to LAN 470) or stored on a publicly accessible network 475, in some examples.

Figure 3A:
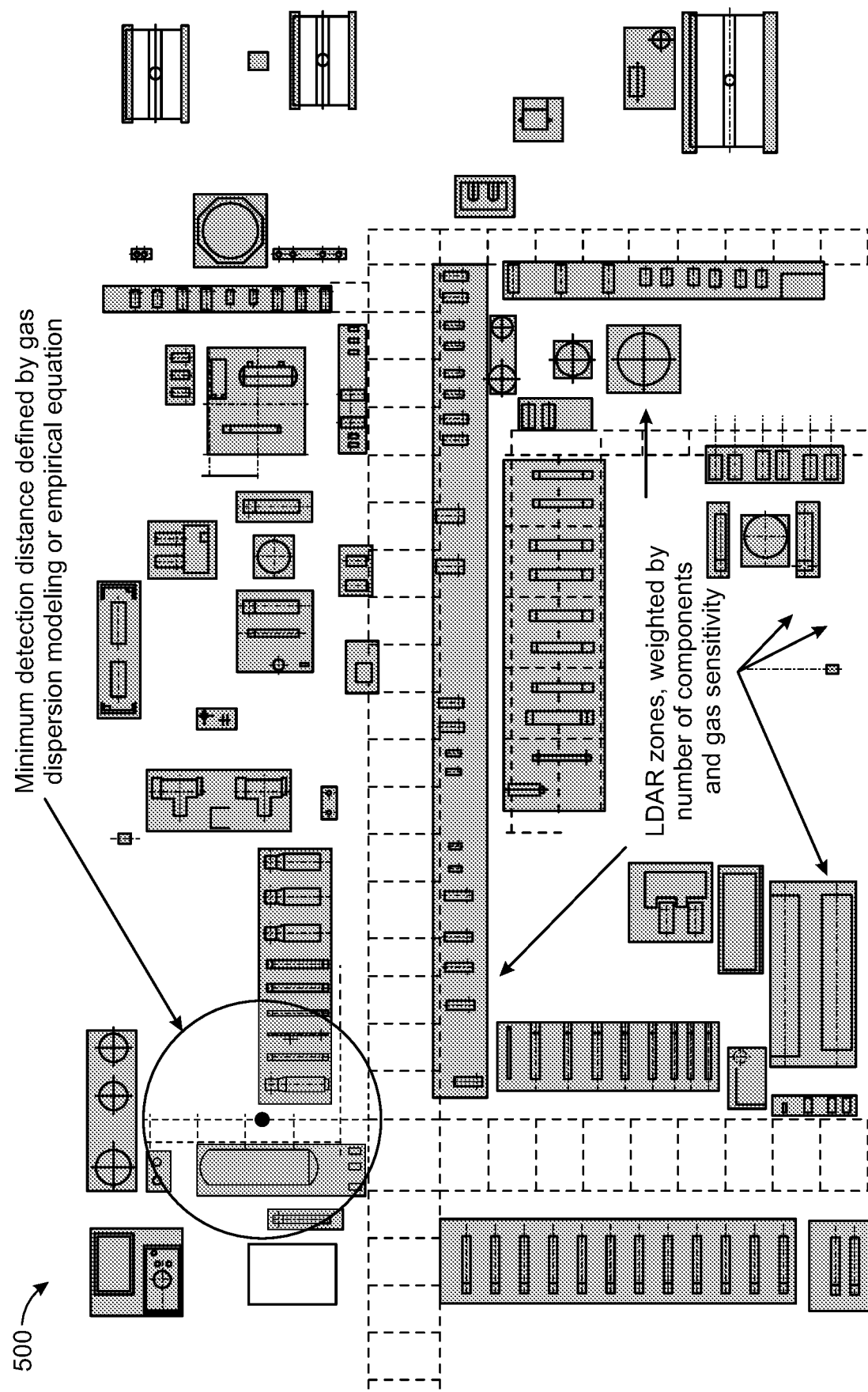
FIG. 3A illustrates a sample two-dimensional layout of a representative facility with identified simulated LDAR zones and optimized locations of detection zones of the sensors in accordance with various aspects of the disclosure.

FIGS. 3A-3D illustrate one example of step 215 in FIG. 1, in which one or more simulated LDAR zones 500 are generated, and the LDAR zones represent the general areas/locations within a facility. In some examples, the LDAR zones may correspond to areas that are subject to LDAR work practices in view of Environmental Protection Agency (EPA) Method 21. In other examples, the LDAR zones may correspond to other EPA methods, not necessarily Method 21. In yet other examples, the LDAR zones may correspond to requirements unrelated to the EPA, but still rely upon an underlying facility layout that comprises components such as buildings, mechanical components, electrical components, electro-mechanical components, and other types of components that cooperate together to serve the functions of the facility. The facility layout is captured into an electronic format that may be layered with one or more LDAR zones 500, as illustrated in FIG. 3A, by grayed rectangular blocks. Any of numerous conventional means for capturing a facility layout may be used in accordance with the embodiments disclosed herein.

FIG. 3A illustrates a sample two-dimensional layout of a representative facility with identified simulated LDAR zones and optimized locations of detection zones of the sensors in accordance with various aspects of the disclosure. The detection zones of a sensor may be depicted by a dot indicating the location of the sensor and a circle to represent the zone within which the sensor is able to detect a gaseous plume. For simplicity, in some examples, the detection zone of each sensor may be depicted by a circle (or sphere in 3-dimensional representations). However, in other examples, the detection zone may be altered to accommodate the one or more structures, obstructions, and/or openings in the facility. For example, in a 3-dimensional digital representation, the height of an obstructing structure may have direct bearing on sensor placement, specifically whether the height of a structure is such that a sensor placed at a location may be futile to detect a gaseous plume originating from the opposite side of the obstructing structure. Moreover, the detection zone of a sensor may be effected by the type of sensor being used, the sensitivity of the sensor to a particular gas compound, and other factors as described herein.

Although FIG. 3A is depicted in two-dimensions in the patent drawing sheets for illustration purposes, the simulated zones may be three-dimensional zones or points (e.g., if the facility has specific known location/elevation of each component within the facility that is subject to LDAR testing), and/or a combination of one or more of points, two-dimensional zones, and three-dimensional zones. The (multi-dimensional) LDAR zones may be in any three-dimensional form but are, in this example, generated in simple rectangular prism (or cylinder or spherical) shape; such shapes are sometimes more convenient to manage mathematically. The two-dimensional LDAR zones may be in any two-dimensional form, but are generated in simple rectangular or circular shape, as illustrated by the gray boxes in FIG. 3A. The three-dimensional LDAR zones generated in step 215 need not necessarily be generated based on substantially solid structures—the generated LDAR zones may be based, in whole or in part, on the information obtained in, or the determinations made in, one or both of steps 205 (including, for example, sub-steps 205A, 205B, 205C and 205F) and/or 210. Step 215 may include one or more of sub-steps 215A and 215B.

In one example, one mechanism or means for capturing a facility layout may be as disclosed in sub-step 205A of FIG. 1. The captured facility layout may include data regarding one or more of the following: two-dimensional drawings and/or three-dimensional CAD models showing the structures within the overall facility; the general width/length/height of such structures; information about the structures themselves, e.g., what they are, what they do, etc.; and information about the physical relationship between the structures, e.g., how closely they are positioned to one another, how large/small they are relative to one another, how tall they are relative to one another, etc. While a three-dimensional model is suitable, the foregoing information (or part of it) may also be provided in unprocessed 3D point cloud or mesh files which are taken by a 3D laser or camera scanning survey.

The LDAR zones 500 may be distributed across portions of the facility. Some areas of the facility layout may be weighted for higher likelihood of a gaseous leak forming. Such LDAR zones may be assigned a weight score based on, among other things, the number of components located in the LDAR zone and/or gas sensitivity. For example, the LDAR zones 500 may be more heavily congregated in areas with a higher weight score. Meanwhile, no LDAR zone may be present in those areas assigned no/little weight score, such as office buildings/trailers/roads/hallways/courtyards/foyers with no components or pipes that could become a source of a leak. In one example, an accessibility factor of a LDAR zone (e.g., column/towers are difficult to access and onto which install; in contrast to open walkable areas) and a noise/sensitivity factor (e.g., steam or heat generate more noise in the data and limit detection) may be considered in the aforementioned calculations. The factors may be general and/or continuous 0-1, rather than simply true/false, as is the case for avoidance allowance areas. However, in some examples, avoidance/allowance areas may also include physical structures and "wind shade" areas, where sensors should not be installed. In other examples, the weighted score may incorporate the number of LDAR components in the zone, leak probability by age/component type, historical patterns of failure, and criticality of detection, and may be assigned based, in whole or in part, on the information obtained in one or more of sub-steps 205A, 205B, 205C and 205F in FIG. 1. In some examples, a weighted score may be assigned to each simulated LDAR zone 500. As can be appreciated, some of the steps/sub-steps in FIG. 1 might not be practical since not all facilities may have geolocation data for individual LDAR components or enough historical leak data to assign reliable leak probability.

In addition, the LDAR zones 500 in FIG. 3A may be effected by allowance areas and avoidance areas in the facility. Some examples of allowance areas include various high elevation platforms (namely, a physical boundary, such as, for example, a flange on a pipe), defined between two areas of responsibility), as identified in step 205A. Some examples of avoidance areas include hallways/walkable and open areas, wind shade zones, three-dimensional zones from step 230, and the places where steam relief and high temperature areas have been identified (by sub-step 205G). Wind shade zones are defined as, for example, areas/volumes that are blocked or substantially immune to wind due to the presence of structures within the facility. As explained with respect to FIG. 1 and sub-step 205A, the wind shade zones can be estimated by utilizing computational fluid dynamics (CFD) calculations and/or an empirical equation or with the use of sensors if sufficient sensors can be appropriately positioned. The CFD model or empirical equation incorporates information obtained in, or determined by, in whole or in part, sub-step 205A (e.g., elevation), sub-step 205E (e.g., wind data) and step 230 (e.g., 3D dimensional zones), referring to FIG. 1. The wind shade zones can be determined with or without gas dispersion modeling, in various embodiments in accordance with this disclosure.

Figure 3B:
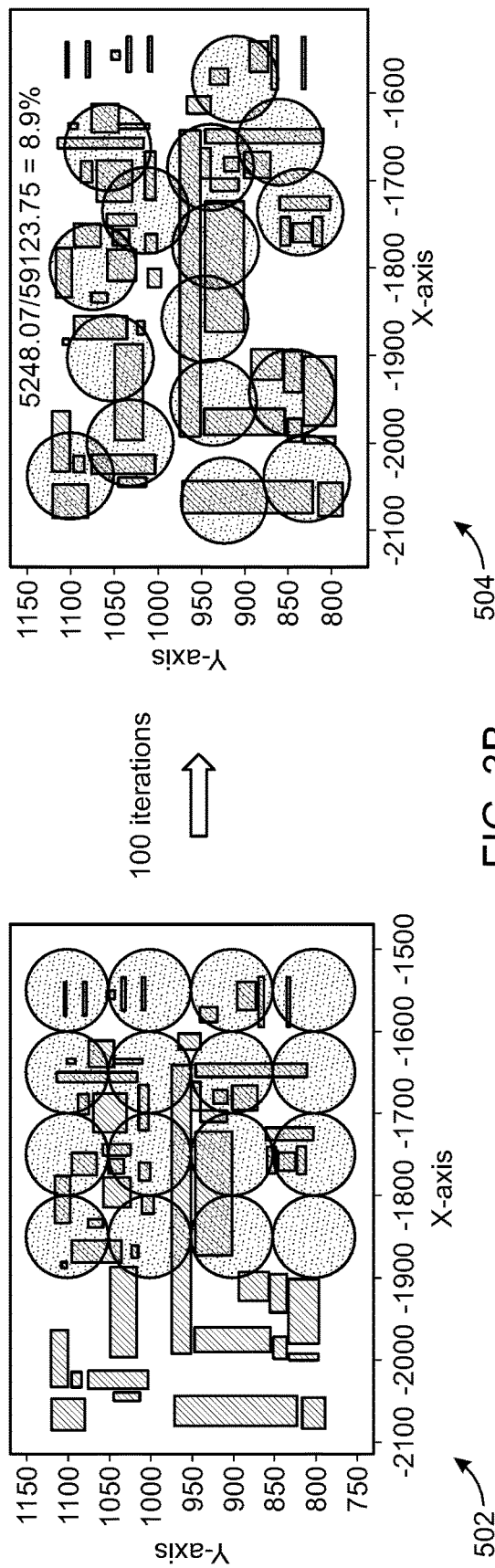
FIG. 3B, FIG. 3C, and FIG. 3D illustrate a before and after of the placement of sensors in a sample two-dimensional layout of a representative facility with identified simulated LDAR zones in accordance with various aspects of the disclosure.
Figure 3C:
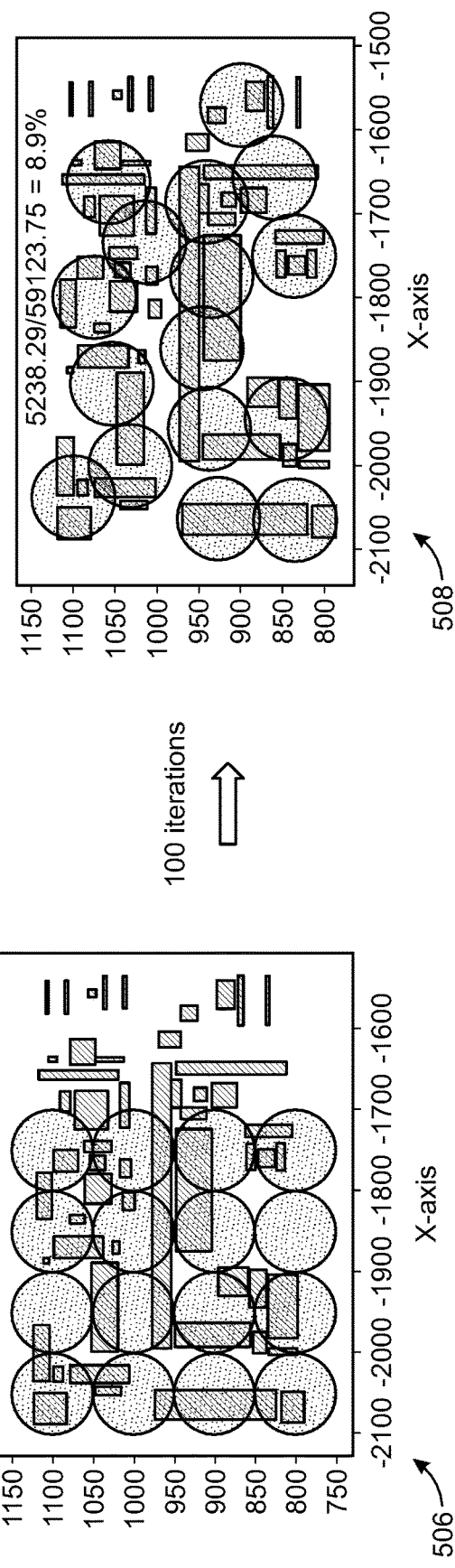
Figure 3D:
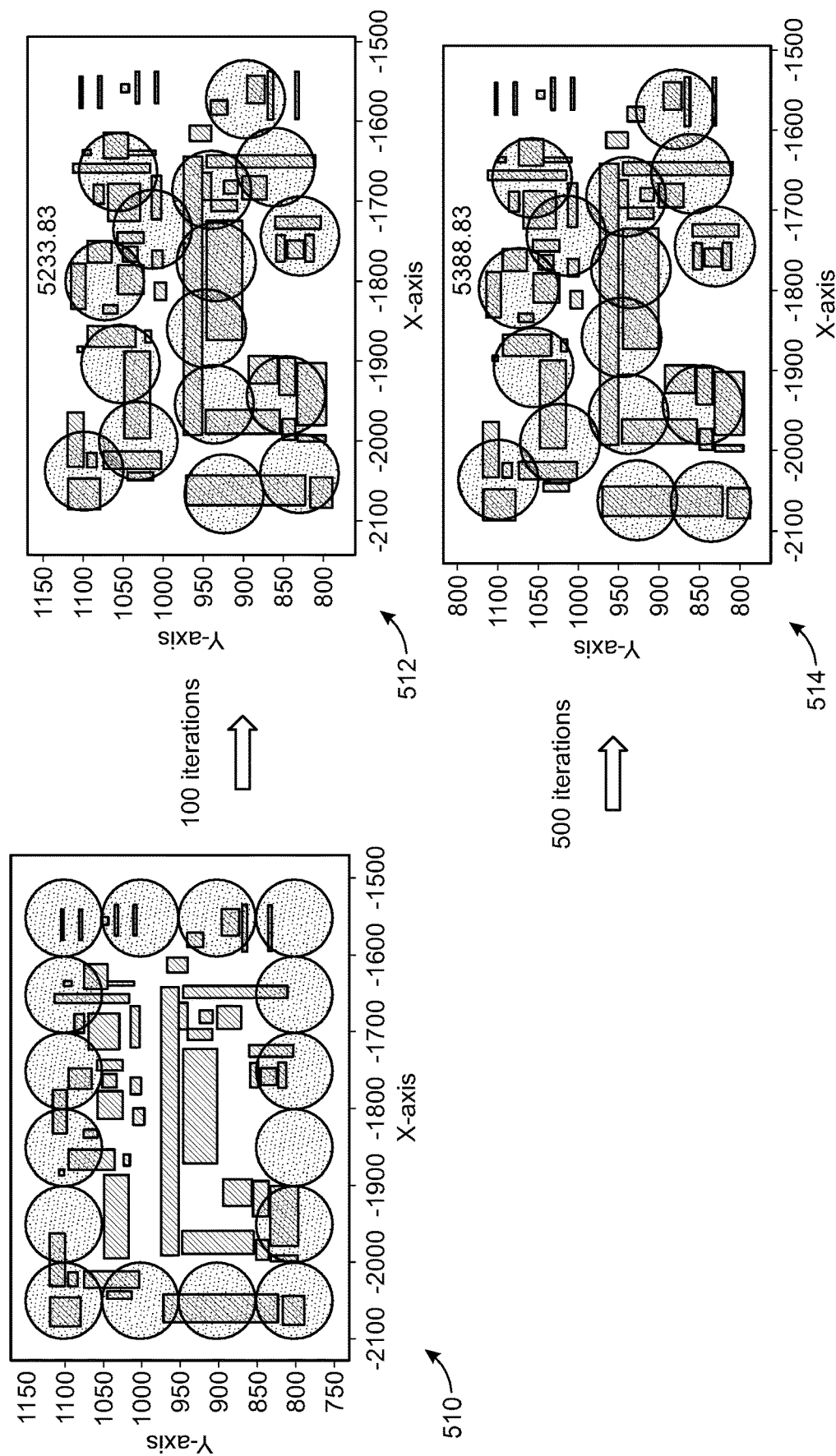

In FIG. 3B, FIG. 3C, and FIG. 3D, the LDAR zones 500 from FIG. 3A are replicated, but with less detailing due to page size constraints. FIG. 3B, FIG. 3C, and FIG. 3D illustrate a before (see 502, 506, 510) and after (504, 508, 512, 514) of the placement of sensors in a digital representation of a two-dimensional layout of a representative facility with identified simulated LDAR zones depicted as grayed rectangles, in accordance with various aspects of the disclosure. The sensors, depicted by circles in FIG. 3B, FIG. 3C, and FIG. 3D, represent a detection area of a sensor located at or near the center of the circle. While the digital representation of the facility may start with the sensors as positioned in 502, 506, or 508, after algorithmically calculating, using artificial intelligence (AI), an optimal placement of the plurality of networked sensors in the digital representation, the placement of the networked sensors may transform into 504, 508, or 512, respectively. In one example, the algorithmic calculating may occur using physics-based equations such as the following related to maximal detection distance (D_max), and then defining detection zones for individual sensors:

$$S_{min} = f_1(L_{min}, X) f_2(D_{max}, \Delta H) f_3(D_{max}, H, \Delta H),$$

Where S_min is minimal detection signal, which defined by the sensor signal-to-noise ratio (SNR) and effectiveness of background correction. And, where L_min is minimal leak size definition per government regulations (EPA for LDAR, OSHA for safety, etc.) or plant specific requirements. And, where $X=f_4(X_1, F_1, X_2, F_2, X_3, F_3, \ldots)$ is an overall gas cross-sensitivity factor for a mix the process chemicals A1, A2, A3 etc. with individual cross-sensitivity factors $X_1$, $X_2$, $X_3$ etc. molar fractions $F_1$, $F_2$, $F_3$ etc. respectively, the cross-sensitivity factor may be defined by sensor technology and type of process chemicals, as explained herein. And, where H is sensor location elevation, and ΔH is elevation difference between sensor and potential leak zone. Moreover, examples of $f_1(L_{min}, X)$, $f_2(x, H)$, and $f_3(x, H, \Delta H)$ may be listed as follows (based on Gaussian plume approximation), where $C_1$, $C_2$ and $C_3$ are constants:

$$f_1(L_{min}, X) \propto L_{min} \times X$$

$$f_2(x, \Delta H) \propto \frac{1}{x^2} e^{\frac{(C_1 + C_2 \times \Delta H)}{x^2}}$$

$$f_3(x, H, \Delta H) \propto 1 + e^{\frac{C_3 \times (H^2 - C_4 \times H \times \Delta H)}{x^2}}$$

where, $C_1$, $C_2$, $C_3$ and $C_4$ are constants and $f_4(X_1, F_1, X_2, F_2, \ldots X_3, F_3) = X_1 F_1 + X_2 F_2 + \cdots + X_n F_n$.

FIG. 3D illustrates that even after extra iterations of the algorithmic calculations, the positions of the networked sensors remain essentially unchanged. In other words, the placement reaches an optimal configuration as depicted in 512 and 514, to detect gaseous plumes resulting from a leak in the facility. In a 3-dimensional digital representation, the optimal placement may be provided as a first coordinate (X1, Y1, Z1), a second coordinate (X2, Y2, Z2), a third coordinate (X3, Y3, Z3), and so on for each of the networked sensors. In an alternative embodiment, coordinates may be two-dimensional as in X1, Y1 where the third coordinate is a predetermined plane.

In one example, the algorithmic calculating, using artificial intelligence, to determine an optimal placement of the plurality of networked sensors in the digital representation may be performed using a cost function. The present disclosure provides a sensor placement method which determines where to place sensors within a facility while minimizing/reducing the number(s) of sensors required to be placed within the facility to accomplish same. The sensor placement method includes obtaining plant layout, gas composition, meteorological conditions and/or other types of information regarding a facility where the sensor system is to be implemented, determining the types of gas and ancillary sensors needed, and generating the minimum detection distances required based on the sensitivities of the sensors to the gas compounds involved, and then calculating the minimal number of sensors required for each sensor type with optimized sensor locations to ensure best coverage of potentially leaking components within the facility.

The following description describes premises and methodology for the value of detection distance (e.g., 50 ft) used in sensor placement. The minimal detection distance may be just one portion of the cost function. The minimal detection distance may determine the size of circles with respect to size and position of LDAR zones in, for example, FIG. 3B, FIG. 3C, and FIG. 3D. The function may comprise a sum of area differences between each LDAR zone and all detection circles. And, weights may be defined as individual multipliers in the sum for each LDAR zone, with default multiplier equal to one. Allowance or avoidance areas may be implemented as geometrical constraints for the optimization results. Vertical sensor overlap minimization, and accessibility and noise/sensitivity factors may be implemented as a penalty terms added to the cost function. And as for the size of the circles, there may be two or more factors in: (1) sensors being close enough to detect the gas concentration above ambient noise; and (2) sensor network must be dense enough so in case of the leak event multiple sensors will respond (e.g., clear peaks above background). The following formulas describe the first factor, but a person having skill in the art after review of the entirety disclosed herein will understand how to make and use formulas for the other factors and elements described herein.

Some plants may use a sensor network for safety monitoring purpose. For this type of applications, local areas where major components are located may be assigned a weight factor based on the probability of leakage, the criticality to safety, and/or impact of potential leaks to the business. For example, pumps are more likely to leak than valves, which are more likely to leak than connects, therefore areas with pumps may have a high weight factor than area with valves and connectors. On the other hand, an area with high density components may have a higher weight than areas with low density areas. Areas close to manned offices or storage tanks may be assigned a higher weight than remote locations, and lastly, areas processing or carrying flammable or high value products may be assigned higher weights, too. With all the information entered into the system and based on overall budget, the method as well as the system disclosed herein is able to generate an optimal sensor placement plan that provides the most value to the plant.

In one example, the aforementioned cost function may be implemented as follows:

$$A = \sum_{i,j} w_{ij} A_{diff}(L_i, D_j)$$

where $w_{ij}$ is a weight factor with a default value, in some examples, of 1. And, where $A_{diff}$ is the area/volume of an object/shape defined by geometrical difference between i-th LDAR zone object/shape ($L_i$) and j-th detection zone object/shape ($D_j$). And, where the strength of the detection signal (measured in mV) effects other variable. And, where the leak rate is measured in sccm. Meanwhile, other variable may be constant values that adjust and/or shift the cost function to appropriately represent the facility; in some examples, the value may be anywhere from 1250 to 2750 (e.g., 1341.1, 2541.1, 2150.4, 2340.4, 2234.1, 2709.1, or other values); and another value may be in the range of 25 to 40 (e.g., 25, 27.4, 29.7, 30.4, 32.7, 39.9, or other values). A person having skill in the art after review of the entirety disclosed herein will appreciate that the values of constants may be tweaked using artificial intelligence, such as machine learning, to determine an ideal value based on the characteristics of the facility including, but not limited to, the geographic location of the facility and the configuration of structures and openings in the facility.

The aforementioned examples of algorithmic calculations use artificial intelligence to determine sensor placement to achieve optimal coverage of leak detection and repair (LDAR) components in a digital representation, as illustrated in FIG. 3D. The algorithmic calculations may be performed using a cost function. The output of the AI determines where sensors should be placed in a facility—including sensor density and geospatial placement locations for sensors. For example, the system may accept inputs such as plant layout, gas data, meteorological data, sensor type and/or sensitivity, etc., and conducts analysis, simulation, and optimization using empirical data, gas properties (e.g. molecular weight, boiling point), and/or gas dispersion models. The output of the system is an optimal placement of the array of networked sensors across the facility—as sensor density determines the sensitivity of the sensor system, the time to catch a new leak, and the ability to differentiate between a new leak and authorized emissions. The system may output instructions specifying where to affix a plurality of networked sensors at specific coordinates in the facility. In one example, the instructions may indicate a first networked sensor is to be affixed at the first coordinate X1, Y1, Z1 in the facility, a second networked sensor is affixed at the second coordinate X2, Y2, Z2 in the facility, and a third networked sensor is affixed at the third coordinate X3, Y3, Z3 in the facility. Of course, while too few sensors are not effective in catching large leaks in time, too many can be a burden to the plant—e.g., conduit installation can be more expensive than the sensors in some classified chemical plants. The cost function identifies an optimization of sensor density based on, inter alia, weight scores assigned to each of the plurality of LDAR zones.

FIG. 4 illustrates that emissions of air pollutants may be reduced if unanticipated emissions that require mitigation can be detected and fixed in a timely manner. From the shared perspective of industrial facilities, workers, regulators, and nearby communities, cost-effective detection and management of fugitive emissions (leaks) is a mutually beneficial concept. In addition to reducing emissions, the disclosure contemplates a safer working environments, reduced resource waste through more efficient work practices and by minimizing/reducing product loss, and improved emissions inventory knowledge and communications with regulators and communities.

Figure 5:
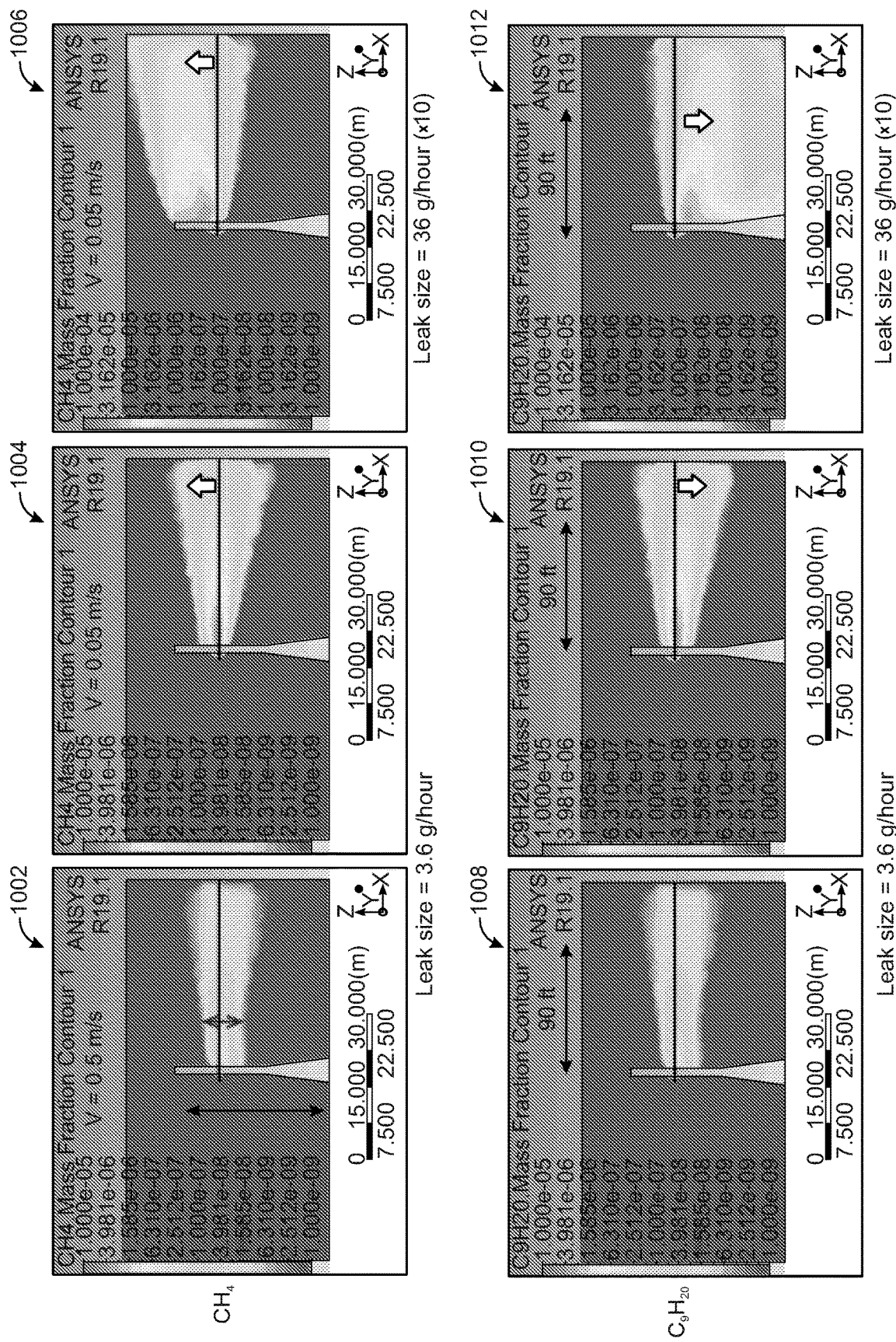
FIG. 5 illustrates sensor measurements from gas plumes of different types of leaks in accordance with various aspects of the disclosure.

FIG. 5 illustrates steady state computational fluid dynamics (CFD) results of a facility in accordance with embodiments disclosed herein. The results 1002, 1004, 1006, 1008, 1010, 1012 show the measurements taken for gas plumes of different types of leaks and under different conditions. For example, a facility transporting CH4 gas will usually generate different sensor measurements than a facility with identical sensors transporting a different gas, such as C9H20 gas. One factor in determining plume width, size, and other characteristics is the type of gas being transmitted through the facility. For example, assuming a leak size of 3.6 g/hour develops in a facility that transports CH4 at a time when the value of wind speed V (measured in meters per second) as measured near the spot in the facility is 0.5 m/s, the resulting width of the gas plume leak would appear narrow, as shown outputted in result 1002. Meanwhile, if the wind speed was V=0.05 m/s with other factors remaining the same, the outputted result 1004 would show a gas plume with a wider width at further distances from the source of the leak. If the leak becomes ten times larger (i.e., 36 g/hour), then the plume result 1004 would change such that the width of the plume is wider at the source and offset from the center of the leak, as illustrated in result 1006.

In another example referring to FIG. 5, if the gas being transmitted through the facility is a different gas, such as C9H20 gas, results 1002, 1004, 1006 may change to results 1008, 1010, 1012, respectively, assuming other factors remain the same. Although measurements 1002 and 1008 appear almost identical, with a different wind speed, the difference between the gaseous plumes becomes more apparent. Result 1010 shows that with a C9H20 gas leak, the width of the plume is offset from the center of the leak in a direction different than that of a CH4 gas leak. The difference between the calculated behavior of the gaseous plumes becomes even more apparent when the leak size is larger, as illustrated in results 1012. Compared to result 1006 with CH4 gas, the measured plume in result 1012 is wider and offset in a different direction.

In some facilities, more than one gaseous material and other materials may be transported simultaneously and/or side-by-side. For example, a facility may have parallel pipes transporting CH4 gas in one pipe and C9H20 gas in another pipe. The system disclosed herein, as illustrated in FIG. 5, may use the same networked sensor to distinguish between a possible CH4 leak gas and a C9H20 gas leak, thus more optimally locate the source of a leak. For example, if a sensor (or networked grid of sensors) output measurement 1012, the system may incorporate that knowledge into identifying a pipe transporting C9H20 gas instead of a pipe transporting CH4 gas.

Although the examples in FIG. 5 reference wind speed, other external, environmental factors may serve to fine tune the emissions monitoring apparatus. For example, in some locations at a facility an accurate wind speed and wind direction measurement may be difficult or impractical to measure. Instead, the test data from the system shows that, in some example, a strong correlation exists between wind speed and temperature. As a result, in some examples, a temperature reading at the location may be used as a substitute, or as a complement, to wind speed measurements. Similarly, the system disclosed herein contemplates that a combination of readings from different types of sensors (such as barometric pressure sensors, humidity sensors, temperature sensors, and other sensors) may be used to arrive at more accurate measurements. Such combination-sensor systems may include one or more sensors that are communicatively coupled to a processor or controller that take the sensor readings as inputs and output a value that more accurately depicts the existing environmental conditions at the location in the facility. In one example, wind speed may be used in triangulation in combination with wind direction. In some examples, the system of FIG. 5 may function with or without a wind speed sensor; however, wind direction may be useful for several example embodiments in this disclosure. The wind direction measurements need not originate solely from sensor assemblies installed at the plant/facility; rather, they can arrive from local meteorological stations and/or Internet. In some examples, wind direction is sampled every one second to ten seconds. In other examples, meteorological measurements may be made by a single or a smaller number of sensor assemblies, rather than by each and every sensor illustrated in FIG. 5.

In one example, an artificial neural network may execute a machine learning algorithm using nonlinear processing or forms of nonlinear processing, in accordance with features described herein.

In one illustrative method using a feedback system of an artificial neural network, the system may use machine learning to determine an output. The output may include a leak area boundary, confidence values, and/or classification output. The system may use an appropriate machine learning model including xg-boosted decision trees, auto-encoders, perceptron, decision trees, support vector machines, regression, and/or a neural network. The neural network may be an appropriate type of neural network including a feed forward network, radial basis network, recurrent neural network, long/short term memory, gated recurrent unit, auto encoder, variational autoencoder, convolutional network, residual network, Kohonen network, and/or other type. In one example, the output data in the machine learning system may be represented as multi-dimensional arrays, an extension of two-dimensional tables (such as matrices) to data with higher dimensionality.

The neural network may include an input layer, a number of intermediate layers, and an output layer. Each layer may have its own weights. The input layer may be configured to receive as input one or more feature vectors described herein. The intermediate layers may be convolutional layers, pooling layers, dense (fully connected) layers, and/or other types. The input layer may pass inputs to the intermediate layers. In one example, each intermediate layer may process the output from the previous layer and then pass output to the next intermediate layer. The output layer may be configured to output a classification or a real value. In one example, the layers in the neural network may use an activation function such as a sigmoid function, a Tanh function, a ReLu function, and/or other functions. Moreover, the neural network may include a loss function. A loss function may, in some examples, measure a number of missed positives; alternatively, it may also measure a number of false positives. The loss function may be used to determine error when comparing an output value and a target value. For example, when training the neural network, the output of the output layer may be used as a prediction and may be compared with a target value of a training instance to determine an error. The error may be used to update weights in each layer of the neural network.

In one example, the neural network may include a technique for updating the weights in one or more of the layers based on the error. The neural network may use gradient descent to update weights. Alternatively, the neural network may use an optimizer to update weights in each layer. For example, the optimizer may use various techniques, or combination of techniques, to update weights in each layer. When appropriate, the neural network may include a mechanism to prevent overfitting—regularization (such as L1 or L2), dropout, and/or other techniques. The neural network may also increase the amount of training data used to prevent overfitting.

In one example, the nodes in an artificial neural network may perform various types of processing, such as discrete computations, computer programs, and/or mathematical functions implemented by a computing device. For example, the input nodes into the artificial neural network may comprise logical inputs of different data sources, such as one or more data servers. The processing nodes of the artificial neural network may comprise parallel processes executing on multiple servers in a data center. And, the output nodes of the artificial neural network may be the logical outputs that ultimately are stored in results data stores, such as the same or different data servers as for the input nodes. Notably, the nodes need not be distinct. For example, two nodes in any two sets may perform the exact same processing. The same node may be repeated for the same or different sets.

Each of the nodes may be connected to one or more other nodes. The connections may connect the output of a node to the input of another node. A connection may be correlated with a weighting value. For example, one connection may be weighted as more important or significant than another, thereby influencing the degree of further processing as input traverses across the artificial neural network. Such connections may be modified such that the artificial neural network may learn and/or be dynamically reconfigured. Though nodes are depicted as having connections only to successive nodes in the artificial neural network, connections may be formed between any nodes. For example, one processing node may be configured to send output to a previous processing node.

The artificial neural network may be configured to effectuate decision-making. Multiple data sets may further refine the decision-making, each looking for further more specific tasks, with each node performing some form of processing which need not necessarily operate in the furtherance of that task. The artificial neural network may then make a prediction. The prediction may be correct or incorrect.

The feedback system may be configured to determine whether or not the artificial neural network made a correct decision. Feedback may comprise an indication of a correct answer and/or an indication of an incorrect answer and/or a degree of correctness (e.g., a percentage). For example, the feedback system may be configured to determine if the prediction was correct and, if so, what percentage of the decision was correct. The feedback system may already know a correct answer, such that the feedback system may train the artificial neural network by indicating whether it made a correct decision. The feedback system may comprise human input, such as an administrator telling the artificial neural network whether it made a correct decision. The feedback system may provide feedback (e.g., an indication of whether the previous output was correct or incorrect) to the artificial neural network via input nodes or may transmit such information to one or more nodes. The feedback system may additionally or alternatively be coupled to a storage such that output is stored. The feedback system may not have correct answers at all, but instead base feedback on further processing.

The artificial neural network may be dynamically modified to learn and provide better input. Based on, for example, previous input and output and feedback from the feedback system, the artificial neural network may modify itself. For example, processing in nodes may change and/or connections may be weighted differently. The modifications may be predictions and/or guesses by the artificial neural network, such that the artificial neural network may vary its nodes and connections to test hypotheses.

The artificial neural network need not have a set number of processing nodes or number of sets of processing nodes, but may increase or decrease its complexity. For example, the artificial neural network may determine that one or more processing nodes are unnecessary or should be repurposed, and either discard or reconfigure the processing nodes on that basis. As another example, the artificial neural network may determine that further processing of all or part of the input is required and add additional processing nodes and/or sets of processing nodes on that basis.

The feedback provided by the feedback system may be mere reinforcement (e.g., providing an indication that output is correct or incorrect, awarding the machine learning algorithm a number of points, or the like) or may be specific (e.g., providing the correct output).

The artificial neural network may be supported or replaced by other forms of machine learning. For example, one or more of the nodes of artificial neural network may implement a decision tree, associational rule set, logic programming, regression model, cluster analysis mechanisms, Bayesian network, propositional formulae, generative models, and/or other algorithms or forms of decision-making. The artificial neural network may effectuate deep learning.

Although several embodiments in this application describe an array of networked sensors, in some embodiments the system may operate with non-networked sensors that operates individually without an array configuration of sensors. In such an embodiment, the single sensor may use artificial intelligence, such as machine learning or Bayesian techniques, with a feedback loop to improve the sensors' accuracy and/or precision over time. In other words, the system may use artificial intelligence, such as supervised and unsupervised machine learning and Bayesian techniques, as described herein, to better predict the boundary of a leak. In addition to measured values from automated means, the system may, in some examples, incorporate expert human input that validates or invalidates the boundary predictions generated by the emissions monitoring apparatus.

While particular embodiments are illustrated in and described with respect to the drawings, it is envisioned that those skilled in the art after review of the entirety disclosed herein may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure and the appended claims. It is to be understood that other embodiments may be utilized and structural and functional modifications may be made without departing from the scope described herein. Further, the foregoing descriptions describe methods that recite the performance of a number of steps. Unless stated to the contrary, one or more steps within a method may not be required, one or more steps may be performed in a different order than as described, and one or more steps may be formed substantially contemporaneously. Various aspects are capable of other embodiments and of being practiced or being carried out in various different ways. It is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof. In addition, although several examples involve the transport of gaseous materials across a distance, the disclosure is not so limited. Rather, chemicals or other forms of VOCs and/or HAPs that are transported across a distance may serve as replacements for gas—for example, the facility/plant may transport chemical liquids/materials that, when leaked, cause a gaseous plume to form.

We claim:

1. A method for placement of a plurality of networked sensors in a facility that transports chemical materials across a distance to detect one or more gaseous plumes resulting from leaks in the facility, the method comprising:
storing, by an emissions monitoring apparatus in a data store, a digital representation of the facility comprising a plurality of components that transport the chemical materials across the distance, wherein the digital representation comprises a plurality of zones spread across the facility;
algorithmically calculating an optimal placement of a plurality of networked sensors in the digital representation of the facility to detect a gaseous plume resulting from a leak, wherein the optimal placement comprises at least a first coordinate, a second coordinate, and a third coordinate;
providing instructions to affix a plurality of networked sensors at specific coordinates in the facility, wherein the instructions indicate a first networked sensor is to be affixed at the first coordinate in the facility, a second networked sensor is to be affixed at the second coordinate in the facility, and a third networked sensor is to be affixed at the third coordinate in the facility; and
updating the first coordinate, the second coordinate, and the third coordinate in the digital representation of the facility stored in the data store with actual coordinates reported to the emissions monitoring apparatus.

2. The method of claim 1, wherein the plurality of components that transport the chemical materials across the distance comprise:
a valve component assembled between a first component and a second component of the plurality of components that transport chemical materials in the facility; and
a controller, which is communicatively coupled to the emissions monitoring apparatus, configured to actuate the valve component from an open position to a closed position;
and the method further comprises:
in response to the second component being identified as a source of the leak, actuating, by the emissions monitoring apparatus, the controller to actuate the valve component into the closed position; and
after the plurality of networked sensors are affixed in the facility, calculating, by the emissions monitoring apparatus, the actual coordinates of each of the first networked sensor, the second networked sensor, and the third networked sensor in the facility by triangulating a wireless signal emitted by each of the first networked sensor, the second networked sensor, and the third networked sensor.

3. The method as claimed in claim 1, further comprising:
generating, by a remote server machine, the digital representation of the facility, wherein the digital representation comprises 3-dimensional structures, 3-dimensional openings between the 3-dimensional structures, a geographic location of the facility, the plurality of components that transport chemical materials across the distance in the facility, and a composition of the chemical materials.

4. The method of claim 1, wherein a first zone of the plurality of zones is assigned a weight score based on at least a quantity of components located in the first zone, gas sensitivity, and one or more parameters comprising:

gas type, gas composition, sensor type, sensor sensitivity, meteorological condition, dimensions of sensor coverage, historical leak data, and leak probability;

and wherein the algorithmically calculating comprises:
iterating through a plurality of combinations of the first coordinate, the second coordinate, and the third coordinate to identify, using artificial intelligence (AI), an optimization of a cost function based on weight scores assigned to each of the plurality of zones, wherein the cost function is based on at least a detection zone of each of the first networked sensor, the second networked sensor, and the third networked sensor; and wherein the optimization is further based on satisfying a pre-defined coverage percentage threshold for one of: individual zones, all zones, and geometric sensor location.

5. The method of claim 1, wherein the plurality of zones comprise LDAR zones.

6. The method as claimed in claim 4, wherein the cost function is further based on:
a sensor type and sensitivity of each of the first networked sensor, the second networked sensor, and the third networked sensor, wherein the detection zone of each networked sensor is derived from its sensor type and sensitivity; and
a composition of the chemical materials transported across the distance in the facility in the plurality of components.

7. The method as claimed in claim 1, wherein the plurality of networked sensors comprises the first networked sensor, the second networked sensor, and the third networked sensor, and wherein the plurality of networked sensors comprise a sensor assembly configured to measure the current meteorological conditions at the facility, and wherein the first networked sensor comprises multiple sensors of more than one type.

8. The method as claimed in claim 1, wherein the algorithmically calculating comprises:
optimizing, using artificial intelligence (AI), a density of the plurality of networked sensors in the digital representation of the facility based on a cost function comprising:

$$A = \sum_{i,j} w_{ij} A_{diff}(L_i, D_j)$$

where $w_{ij}$ is a weight factor with a default value, and wherein $A_{diff}$ is an area of an object defined by geometrical difference between i-th LDAR zone object ($L_i$) and j-th detection zone object ($D_j$).

9. The method as claimed in claim 1, further comprising:
after the plurality of networked sensors are affixed in the facility, calculating, by the emissions monitoring apparatus, the actual coordinates of each of the first networked sensor, the second networked sensor, and the third networked sensor in the facility by triangulating a wireless signal emitted by each of the first networked sensor, the second networked sensor, and the third networked sensor,
wherein the triangulating the wireless signal comprises calculating time to receive the wireless signal.

10. The method as claimed in claim 1, wherein the algorithmically calculating comprises:
excluding the plurality of networked sensors from coordinates in avoidance areas in the facility.

11. A system for placement and monitoring of a plurality of networked sensors in a facility that transports materials across a distance, the system comprising:
a plurality of networked sensors configured to detect one or more gaseous plumes resulting from leaks in the facility;
a data store configured to store a digital representation of the facility, wherein the digital representation comprises a plurality of components that transport the materials across the distance and a plurality of zones spread across the facility; and
an emissions monitoring apparatus comprising a processor and a memory storing computer-executable instructions that, when executed by the processor, cause the system to perform steps comprising:
algorithmically calculating, by the processor, an optimal placement of the plurality of networked sensors in the digital representation of the facility to detect a gaseous plume resulting from a leak, wherein the optimal placement comprises at least a first coordinate, a second coordinate, and a third coordinate;
providing instructions, by the emissions monitoring apparatus, to affix the plurality of networked sensors at specific coordinates in the facility, wherein the instructions indicate a first networked sensor is to be affixed at the first coordinate in the facility, a second networked sensor is to be affixed at the second coordinate in the facility, and a third networked sensor is to be affixed at the third coordinate in the facility; and
updating, by the emissions monitoring apparatus, the first coordinate, the second coordinate, and the third coordinate in the digital representation of the facility stored in the data store with actual coordinates calculated by the emissions monitoring apparatus.

12. The system of claim 11, wherein the memory of the emissions monitoring apparatus stores further computer-executable instructions that, when executed by the processor, cause the system to perform steps comprising:
after the plurality of networked sensors are affixed in the facility, calculating, by the emissions monitoring apparatus, the actual coordinates of each of the first networked sensor, the second networked sensor, and the third networked sensor in the facility by triangulating a wireless signal emitted by each of the first networked sensor, the second networked sensor, and the third networked sensor,
wherein the triangulating the wireless signal comprises calculating time to receive the wireless signal.

13. The system of claim 11, wherein each of the plurality of zones is assigned a weight score based on at least a quantity of components located in that zone, gas sensitivity, and one or more parameters comprising:
gas type, gas composition, sensor type, sensor sensitivity, meteorological condition, dimensions of sensor coverage, historical leak data, and leak probability.

14. The system as claimed in claim 11, wherein the plurality of zones comprise LDAR zones, and wherein a first zone of the plurality of zones is assigned a weight score based on at least a quantity of components located in the first zone and gas sensitivity, and wherein the algorithmically calculating comprises:
iterating through a plurality of combinations of the first coordinate, the second coordinate, and the third coordinate to identify, using artificial intelligence (AI), an optimization of a cost function based on weight scores assigned to each of the plurality of LDAR zones, wherein the cost function is based on at least a detection zone of each of the first networked sensor, the second networked sensor, and the third networked sensor; and wherein the optimization also is based on satisfying a pre-defined coverage percentage threshold for one of: individual LDAR zones, all LDAR zones, and geometric sensor location.

15. The system as claimed in claim 11, wherein the materials being transported across the distance comprise chemical materials, and wherein the data store is a part of the memory of the emissions monitoring apparatus, and wherein the memory of the emissions monitoring apparatus stores further computer-executable instructions that, when executed by the processor, cause the system to perform steps comprising:
   storing, by the processor in the data store, the digital representation of the facility.

16. The system as claimed in claim 11, wherein the plurality of networked sensors comprise a sensor assembly configured to measure the current meteorological conditions at the facility, and wherein the first networked sensor comprises multiple sensors of more than one type, wherein the algorithmically calculating comprises:
   optimizing, using artificial intelligence (AI), a density of the plurality of networked sensors in the digital representation of the facility based on a cost function comprising:

$$A = \sum_{i,j} w_{ij} A_{diff}(L_i, D_j)$$

where $w_{ij}$ is a weight factor with a default value, and wherein $A_{diff}$ is an area of an object defined by geometrical difference between i-th LDAR zone object ($L_i$) and j-th detection zone object ($D_j$).

17. A non-transitory computer-readable medium storing computer-executable instructions that, when executed by a processor, cause a system to detect a gaseous plume resulting from a leak in a facility by performing steps comprising:
   storing, in a data store, a digital representation of a facility comprising a plurality of components that transport chemical materials across a distance, wherein the digital representation comprises a plurality of zones spread across the facility, and wherein each zone of the plurality of zones is assigned a weight score based on at least a quantity of components located in its zone and gas sensitivity;
   algorithmically calculating an optimal placement of a plurality of networked sensors in the digital representation of the facility by iterating through a plurality of combinations of coordinates for each of the plurality of networked sensors to identify, using artificial intelligence (AI), an optimization of a cost function based on weight scores assigned to each of the plurality of zones, wherein the cost function is based on at least a detection zone of each of the plurality of networked sensors, and wherein the optimization is further based on satisfying a pre-defined coverage percentage threshold for one of: individual zones, all zones, and geometric sensor location;
   providing instructions to affix the plurality of networked sensors at specific coordinates in the facility, wherein the instructions indicate a first networked sensor is to be affixed at a first coordinate in the facility, a second networked sensor is to be affixed at a second coordinate in the facility, and a third networked sensor is to be affixed at a third coordinate in the facility;
   measuring, in near real-time at the facility, a current meteorological condition at the facility; and
   updating the digital representation of the facility stored in the data store using the current meteorological condition and the specific coordinates in the facility to which the plurality of networked sensors is affixed.

18. The non-transitory computer-readable medium of claim 17, wherein the current meteorological conditions comprise wind speed, wind direction, and temperature.

19. The non-transitory computer-readable medium as claimed in claim 17, further storing computer-executable instructions that, when executed by the processor, cause the system to perform steps comprising:
   after the plurality of networked sensors are affixed in the facility, calculating, by the emissions monitoring apparatus, the actual coordinates of each of the plurality of networked sensors in the facility by triangulating a wireless signal emitted by each of the plurality of networked sensors.

20. The non-transitory computer-readable medium as claimed in claim 17, wherein the cost function is further based on:
   a sensor type and sensitivity of each of the first networked sensor, the second networked sensor, and the third networked sensor, wherein the detection zone of each networked sensor is derived from at least its sensor type, sensitivity, and one or more parameters comprising: gas type, gas composition, sensor type, sensor sensitivity, meteorological condition, dimensions of sensor coverage, historical leak data, and leak probability; and
   a composition of the chemical materials transported across the distance in the facility in the plurality of components.

* * * * *